(12) United States Patent
Chapdelaine et al.

(10) Patent No.: US 7,566,727 B2
(45) Date of Patent: Jul. 28, 2009

(54) 2-(1-AZA-BICYCLO[2.2.2]OCT-3-YL)-2,3-DIHYDRO-ISOINDOLE-1-ONE/5,6-DIHYDRO-FURO[2,3-C] PYRROL-4-ONE DERIVATIVE LIGANDS FOR ALPHA 7 NICOTINIC ACETYLCHOLINE RECEPTOR

(75) Inventors: Marc Chapdelaine, Wilmington, DE (US); Keith J. Herzog, Wilmington, DE (US)

(73) Assignee: AstraZeneca AB, Sodertalje ( * ) Notice: Subject to any disclaimer, the term of this patent is extended or adjusted under 35 U.S.C. 154(b) by 279 days.

(21) Appl. No.: 10/599,839

(22) PCT Filed: Apr. 6, 2005

(86) PCT No.: PCT/SE2005/000500

§ 371 (c)(1),
(2), (4) Date: Oct. 11, 2006

(87) PCT Pub. No.: WO2005/100351

PCT Pub. Date: Oct. 27, 2005

(65) Prior Publication Data

US 2007/0213342 A1 Sep. 13, 2007

(30) Foreign Application Priority Data

Apr. 14, 2004 (SE) .................................... 0400970

(51) Int. Cl.
*A01N 43/90* (2006.01)
*C07D 453/02* (2006.01)

(52) U.S. Cl. .................. 514/305; 546/133; 546/137

(58) Field of Classification Search ................ 546/133, 546/137; 514/305

See application file for complete search history.

(56) References Cited

U.S. PATENT DOCUMENTS 5,491,148 A 2/1996 Berger et al.

FOREIGN PATENT DOCUMENTS

| EP | 1018512 A1 | 7/2000 |
|---|---|---|
| WO | 9323395 A1 | 11/1993 |
| WO | 0220521 A1 | 3/2002 |
| WO | 0244176 A1 | 6/2002 |
| WO | 02083640 A1 | 10/2002 |
| WO | 03004493 A1 | 1/2003 |
| WO | 2004016608 A1 | 2/2004 |

OTHER PUBLICATIONS

Cappelli et al., Bioorganic & Medicinal Chemistry (2002), 10(3), 779-801.*
Ffrench-Constant et al., Journal of Neurochemistry (1992), 59(4), 1562-5).*
Capelli, Andrea et al, "Novel Potent 5-HT3 Receptor Ligands Based . . . Modalities", Bioorganic & Medicinal Chemistry, Mar. 2002, vol. 10, Issue 3, pp. 779-801.

* cited by examiner

*Primary Examiner*—D. Margaret Seaman
*Assistant Examiner*—Niloofar Rahmani
(74) *Attorney, Agent, or Firm*—Kenneth F. Mitchell

(57) ABSTRACT

This invention encompasses nicotinic acetylcholine receptor reactive compounds in accord with formula (I) Wherein: D represents O; E represents CH2, NH, O or S; n is 1 or 2 and stereoisomers, enantiomers, in vivo-hydrolysable precursors and pharmaceutically-acceptable salts of such compounds, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

9 Claims, No Drawings

2-(1-AZA-BICYCLO[2.2.2]OCT-3-YL)-2,3-DIHYDRO-ISOINDOLE-1-ONE/ 5,6-DIHYDRO-FURO[2,3-C] PYRROL-4-ONE DERIVATIVE LIGANDS FOR ALPHA 7 NICOTINIC ACETYLCHOLINE RECEPTOR

CROSS-REFERENCE TO RELATED APPLICATIONS

This application is a US National Stage under 35 U.S.C. § 371 of International Application No. PCT/SE2005/000500 (filed Apr. 6, 2005) that claims priority under 35 U.S.C. § 119(a)-(d) to Application No. 0400970-0 filed in Sweden on Apr. 14, 2004.

TECHNICAL FIELD

This invention relates to novel isoindolones or pharmaceutically-acceptable salts thereof, processes for preparing them, pharmaceutical compositions containing them and their use in therapy. This invention particularly relates to isoindolone compounds that are ligands for alpha 7 nicotinic acetylcholine receptors (α7 nAChRs).

BACKGROUND OF THE INVENTION

The use of compounds which bind nicotinic acetylcholine receptors in the treatment of a range of disorders involving reduced cholinergic function, such as anxiety, depression, schizophrenia, cognitive or attention disorders, Alzheimer's disease, Parkinson's disease, Tourette's syndrome, and for facilitating smoking cessation, for providing neuroprotection and inducing analgesia, has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; and in Williams et al. (1994) "Neuronal Nicotinic Acetylcholine Receptors," Drug News & Perspectives, Vol. 7, pp. 205-223.

DESCRIPTION OF THE INVENTION

This invention encompasses nicotinic acetylcholine receptor-reactive compounds in accord with formula I:

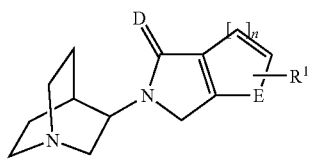

I wherein:
D represents O;
E represents $CH_2$, NH, O or S;
n is 1 or 2 and
$R^1$ is selected from hydrogen, halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —$CF_3$, —$S(O)_mR^2$ wherein m is 0, 1 or 2, —$NR^2R^3$, —$NR^2C(O)R^3$, —$CH_2NR^2R^3$, $OR^2$, —$CH_2OR^2$, —$C(O)NR^2R^3$, or —$CO_2R^4$;
$R^2$ and $R^3$ are independently selected at each occurrence from hydrogen, —$C_1$-$C_4$alkyl, —$C_1$-$C_4$alkoxy, —$C_3$-$C_6$cycloalkyl, aryl, heteroaryl, —$C(O)R^4$, —$CO_2R^4$ or —$SO_2R^4$, or
$R^2$ and $R^3$ in combination is —$(CH_2)_jG(CH_2)_k$— or -$G(CH_2)_j$G- wherein G is oxygen, sulfur, $NR^4$, or a bond, j is 0, 1, 2, 3 or 4 and k is 0, 1, 2, 3 or 4, and
$R^4$ is independently selected at each occurrence from hydrogen, —$C_1$-$C_4$alkyl, aryl, or heteroaryl.

Particular compounds of the invention are nicotinic acetylcholine receptor-reactive compounds in accord with formula II or III:

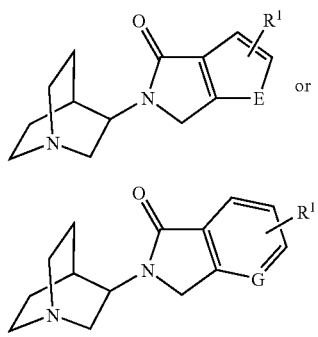

II or

III wherein:
E represents or $CH_2$, NH, O or S;
G represents CH or N;
$R^1$ is selected from hydrogen, halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —$CF_3$, —$S(O)_mR^2$ wherein m is 0, 1 or 2, —$NR^2R^3$, —$NR^2(CO)R^3$, —$CH_2NR^2R^3$, $OR^2$, —$CH_2OR^2$, —$C(O)NR^2R^3$, or —$CO_2R^4$;
$R^2$ and $R^3$ are independently selected at each occurrence from hydrogen, —$C_1$-$C_4$alkyl, —$C_1$-$C_4$alkoxy, —$C_3$-$C_6$cycloalkyl, aryl, heteroaryl, —$C(O)R^4$, —$CO_2R^4$ or —$SO_2R^4$, or
$R^2$ and $R^3$ in combination is —$(CH_2)_jG(CH_2)_k$— or -$G(CH_2)_j$G- wherein G is oxygen, sulfur, $NR^4$, or a bond, j is 0, 1, 2, 3 or 4 and k is 0, 1, 2, 3 or 4, and
$R^4$ is independently selected at each occurrence from hydrogen, —$C_1$-$C_4$alkyl, aryl, or heteroaryl.

The invention also encompasses stereoisomers, enantiomers, in vivo-hydrolysable precursors and pharmaceutically-acceptable salts of compounds of formula II or III, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

Particular compounds of the invention are nicotinic acetylcholine receptor-reactive compounds in accord with formula II:

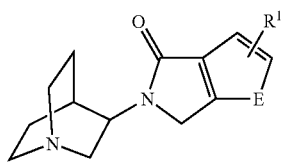

wherein:

E represents or $CH_2$, NH, O or S;

$R^1$ is selected from hydrogen, halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —$CF_3$, —$S(O)_mR^2$ wherein m is 0, 1 or 2, —$NR^2R^3$, —$NR^2(CO)R^3$, —$CH_2NR^2R^3$, $OR^2$, —$CH_2OR^2$, —$C(O)NR^2R^3$, or —$CO_2R^4$;

$R^2$ and $R^3$ are independently selected at each occurrence from hydrogen, —$C_1$-$C_4$alkyl, —$C_1$-$C_4$alkoxy, —$C_3$-$C_6$cycloalkyl, aryl, heteroaryl, —$C(O)R^4$, —$CO_2R^4$ or —$SO_2R^4$, or $R^2$ and $R^3$ in combination is —$(CH_2)_jG(CH_2)_k$— or -$G(CH_2)_jG$- wherein G is oxygen, sulfur, $NR^4$, or a bond, j is 0, 1, 2, 3 or 4 and k is 0, 1, 2, 3 or 4, and $R^4$ is independently selected at each occurrence from hydrogen, —$C_1$-$C_4$alkyl, aryl, or heteroaryl;

stereoisomers, enantiomers, in vivo-hydrolysable precursors and pharmaceutically-acceptable salts thereof.

Other compounds of the invention are nicotinic acetylcholine receptor-reactive compounds in accord with formula III:

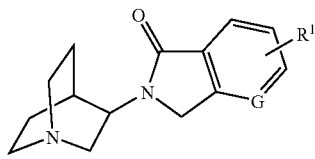

wherein:

G represents CH or N;

$R^1$ is selected from hydrogen, halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —$CF_3$, —$S(O)_mR^2$ wherein m is 0, 1 or 2, —$NR^2R^3$, —$NR^2(CO)R^3$, —$CH_2NR^2R^3$, $OR^2$, —$CH_2OR^2$, —$C(O)NR^2R^3$, or —$CO_2R^4$;

$R^2$ and $R^3$ are independently selected at each occurrence from hydrogen, —$C_1$-$C_4$alkyl, —$C_1$-$C_4$alkoxy, —$C_3$-$C_6$cycloalkyl, aryl, heteroaryl, —$C(O)R^4$, —$CO_2R^4$ or —$SO_2R^4$, or $R^2$ and $R^3$ in combination is —$(CH_2)_jG(CH_2)_k$— or -$G(CH_2)_jG$- wherein G is oxygen, sulfur, $NR^4$, or a bond, j is 0, 1, 2, 3 or 4 and k is 0, 1, 2, 3 or 4, and $R^4$ is independently selected at each occurrence from hydrogen, —$C_1$-$C_4$alkyl, aryl, or heteroaryl;

stereoisomers, enantiomers, in vivo-hydrolysable precursors and pharmaceutically-acceptable salts thereof.

Particular compounds of the invention are those in accord with formula II or III, wherein, $R^1$ is selected from hydrogen, halogen and substituted or unsubstituted phenyl, pyridyl, quinolinyl, piperazinyl or morpholinyl, said phenyl, pyridyl, quinolinyl, piperazinyl or morpholiny, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —$CF_3$, —$S(O)_mR^2$ wherein m is 0, 1 or 2, —$NR^2R^3$, —$CH_2NR^2R^3$, —$OR^2$, —$CH_2OR^2$ or —$CO_2R^4$.

Particular compounds of the invention are R-stereoisomers of compounds of formula II or III in accord with formula IV or V,

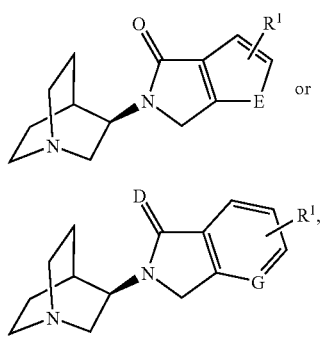

wherein E, G and $R^1$ are as defined herein.

Particular compounds of the invention are those described herein and pharmaceutically-acceptable salts thereof.

In a further aspect the invention relates to compounds described herein wherein one or more of the atoms is a radio-isotope of the same element. In a particular form of this aspect of the invention the compound is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Compounds of the invention labeled with tritium are useful for the discovery of novel medicinal compounds which bind to and modulate the activity, by agonism, partial agonism, or antagonism, of the α7 nicotinic acetylcholine receptor. Such tritium-labeled compounds may be used in assays that measure the displacement of such compounds to assess the binding of ligands that bind to α7 nicotinic acetylcholine receptors.

In a further aspect the invention relates to compounds described herein additionally comprising one or more atoms of a radioisotope. In a particular form of this aspect of the invention the compound comprises a radioactive halogen. Such radio-labeled compounds are synthesized by incorporating radio-labeled starting materials by known methods. Particular embodiments of this aspect of the invention are those in which the radioisotope is selected from $^{18}F$, $^{123}I$, $^{125}I$, $^{131}I$, $^{75}Br$, $^{76}Br$, $^{77}Br$ or $^{82}Br$. A most particular embodiment of this aspect of the invention is that in which the radioisotope is $^{18}F$.

In another aspect the invention relates to compounds described herein and their use in therapy and to compositions containing them.

In another aspect the invention encompasses the use of compounds described herein for the therapy of diseases mediated through the action of nicotinic acetylcholine receptors. A more particular aspect of the invention relates to the use of the compounds for the therapy of diseases mediated through the action of α7 nicotinic acetylcholine receptors.

Another aspect of the invention encompasses a method of treatment or prophylaxis of diseases or conditions in which activation of the α7 nicotinic receptor is beneficial which method comprises administering a therapeutically-effective amount of a compound of the invention to a subject suffering from said disease or condition.

One embodiment of this aspect of the invention is a method of treatment or prophylaxis, wherein the disorder is anxiety, schizophrenia, mania or manic depression.

Another embodiment of this aspect of the invention is a method of treatment or prophylaxis of neurological disorders, psychotic disorders or intellectual impairment disorders, which comprises administering a therapeutically effective amount of a compound of the invention.

Another embodiment of this aspect of the invention is a method of treatment or prophylaxis, wherein the disorder is Alzheimer's disease, learning deficit, cognition deficit, attention deficit, memory loss, or Attention Deficit Hyperactivity Disorder.

Another embodiment of this aspect of the invention is a method of treatment or prophylaxis, wherein the disorder is Parkinson's disease, Huntington's disease, Tourette's syndrome, or neurodegenerative disorders in which there is loss of cholinergic synapses.

Another embodiment of this aspect of the invention is a method of treatment or prophylaxis of jetlag, nicotine addiction, craving, pain, and for ulcerative colitis, which comprises administering a therapeutically effective amount of a compound of the invention.

Yet another embodiment of this aspect of the invention is a method for inducing the cessation of smoking which comprises administering an effective amount of a compound of the invention.

Another embodiment of this aspect of the invention is a pharmaceutical composition comprising a compound of the invention and a pharmaceutically-acceptable diluent, lubricant or carrier.

A further aspect of the invention relates to a pharmaceutical composition useful for treating or preventing a condition or disorder mentioned herein arising from dysfunction of nicotinic acetylcholine receptor neurotransmission in a mammal, preferably a human, comprising an amount of a compound of the invention, an enantiomer thereof or a pharmaceutically-acceptable salt thereof, effective in treating or preventing such disorder or condition, and pharmaceutically-acceptable additives carrier.

Another embodiment of this aspect of the invention relates to use of a pharmaceutical composition of the invention for the treatment, amelioration or prophylaxis of human diseases or conditions in which activation of the α7 nicotinic receptor is beneficial.

Another embodiment of this aspect of the invention is the use of the pharmaceutical composition of the invention for the treatment or prophylaxis of neurological disorders, psychotic disorders or intellectual impairment disorders.

Another embodiment of this aspect of the invention is the use of the pharmaceutical composition of the invention for the treatment or prophylaxis of Alzheimer's disease, learning deficit, cognition deficit, attention deficit, memory loss, Attention Deficit Hyperactivity Disorder, anxiety, schizophrenia, or mania or manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect of the invention is the use of a compound according to the invention, an enantiomer thereof or a pharmaceutically-acceptable salt thereof, in the manufacture of a medicament for the treatment or prophylaxis of the diseases or conditions mentioned herein.

Another embodiment of this aspect of the invention is the use of a compound of the invention in the manufacture of a medicament for the treatment or prophylaxis of human diseases or conditions in which activation of the α7 nicotinic receptor is beneficial.

Another embodiment of this aspect of the invention is the use of a compound of the invention in the manufacture of a medicament for the treatment or prophylaxis of neurological disorders, psychotic disorders or intellectual impairment disorders.

Another embodiment of this aspect of the invention is the use of a compound of the invention in the manufacture of a medicament for treatment or prophylaxis of Alzheimer's disease, learning deficit, cognition deficit, attention deficit, memory loss or Attention Deficit Hyperactivity Disorder.

Another embodiment of this aspect of the invention is the use of a compound of the invention in the manufacture of a medicament for treatment or prophylaxis of anxiety, schizophrenia, or mania or manic depression.

Another embodiment of this aspect of the invention is the use of a compound of the invention in the manufacture of a medicament for treatment or prophylaxis of Parkinson's disease, Huntington's disease, Tourette's syndrome, or neurodegenerative disorders in which there is loss of cholinergic synapses.

Another embodiment of this aspect of the invention is the use of a compound as described above in the manufacture of a medicament for the treatment or prophylaxis of jetlag, pain, or ulcerative colitis.

Another aspect of the invention relates to the use of a compound of the invention in the manufacture of a medicament for facilitating the cessation of smoking or the treatment of nicotine addiction or craving including that resulting from exposure to products containing nicotine.

For the uses, methods, medicaments and compositions mentioned herein the amount of compound used and the dosage administered will, of course, vary with the compound employed, the mode of administration and the treatment desired. However, in general, satisfactory results are obtained when the compounds of the invention are administered at a daily dosage of about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carriers, lubricants and diluents.

Compounds of the invention, enantiomers thereof, and pharmaceutically-acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically-acceptable diluent, lubricant or carrier.

Examples of diluents, lubricants and carriers are:
  for tablets and dragees: lactose, starch, talc, stearic acid;
  for capsules: tartaric acid or lactose;
  for injectable solutions: water, alcohols, glycerin, vegetable oils;
  for suppositories: natural or hardened oils or waxes.

There is also provided a process for the preparation of such a pharmaceutical composition which process comprises mixing or compounding the ingredients together and forming the mixed ingredients into tablets or suppositories, encapsulating the ingredients in capsules or dissolving the ingredients to form injectable solutions.

Compounds according to the invention are agonists of nicotinic acetylcholine receptors. While not being limited by theory, it is believed that agonists of the α7 nicotinic acetylcholine receptor (nAChR) subtype are useful in the treatment or prophylaxis of neurological disorders, psychotic disorders and intellectual impairment disorders, and to have advantages over compounds which are or are also agonists of the α4 nAChR subtype. Therefore, compounds which are selective for the α7 nAChR subtype are preferred. The compounds of the invention are indicated as pharmaceuticals, in particular in the treatment or prophylaxis of neurological disorders, mood disorders, psychotic disorders and intellectual impairment disorders. Examples of psychotic disorders include schizophrenia, mania and manic depression, and anxiety. Examples of intellectual impairment disorders include Alzheimer's disease, learning deficit, cognition deficit, attention deficit, memory loss, and Attention Deficit Hyperactivity Disorder. The compounds of the invention may also be useful as analgesics in the treatment of pain, chronic pain, and in the treatment or prophylaxis of Parkinson's disease, Huntington's disease, Tourette's syndrome, and neurodegenerative disorders in which there is loss of cholinergic synapses.

Compounds of the invention may further be useful for the treatment or prophylaxis of jetlag, for use in inducing the cessation of smoking, craving, and for the treatment or prophylaxis of nicotine addiction including that resulting from exposure to products containing nicotine.

It is also believed that compounds according to the invention are useful in the treatment and prophylaxis of ulcerative colitis.

The compounds of the invention have the advantage that they may be less toxic, be more efficacious, be longer acting, have a broader range of activity, be more potent, produce fewer side effects, are more easily absorbed or have other useful pharmacological properties.

The compounds of the invention exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Pharmaceutically-acceptable derivatives include solvates and salts. For example, the compounds of the invention can form acid addition salts with acids, such as the conventional pharmaceutically-acceptable acids, for example, maleic, hydrochloric, hydrobromic, phosphoric, acetic, fumaric, salicylic, citric, lactic, mandelic, tartaric and methanesulfonic acids.

PHARMACOLOGY

The pharmacological activity of the compounds of the invention may be measured in the tests set out below:

Test A—Assay for Affinity at $\alpha_7$ nAChR subtype

125I-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12,000 g, washed, and re-suspended in HB. Membranes (30-80 μg) were incubated with 5 nM [$^{125}$I] α-BTX, 1 mg/mL BSA (bovine serum albumin), test drug, and either 2 mM CaCl2 or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pre-treating the filters for 3 hours with 1% (BSA/0.01% PEI (polyethyleneimine) in water was critical for low filter blanks (0.07% of total counts per minute). Non-specific binding was described by 100 μM (−)-nicotine, and specific binding was typically 75%.

Test B—Assay for affinity to the $\alpha_4$ nAChR subtype

[$^3$H]-(−)-nicotine binding. Using a procedure modified from Martino-Barrows and Kellar (Mol Pharm (1987) 31:169-174), rat brain (cortex and hippocampus) was homogenized as in the [$^{125}$I] α-BTX binding assay, centrifuged for 20 minutes at 12,000×g, washed twice, and then re-suspended in HB containing 100 μM diisopropyl fluorophosphate. After 20 minutes at 4° C., membranes (approximately 0.5 mg) were incubated with 3 nM [$^3$H] -(−)-nicotine, test drug, 1 μM atropine, and either 2 mM $CaCl_2$ or 0.5 mM EGTA for 1 hour at 4° C., and then filtered over Whatman glass fibre filters (thickness C) (pre-treated for 1 hour with 0.5% PEI) using a Brandel cell harvester. Non-specific binding was described by 100 μM carbachol, and specific binding was typically 84%.

Binding data analysis for Tests A and B $IC_{50}$ values and pseudo Hill coefficients ($n_H$) were calculated using the non-linear curve fitting program ALLFIT (De- Lean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding $K_D$ values of 1.67 and 1.70 nM for the [$^{125}$I]-α-BTX and [$^3$H]-(−)-nicotine ligands respectively. $K_i$ values were estimated using the general Cheng-Prusoff equation:

$$K_i = [IC_{50}]/((2+([ligand]/K_D])^n)^{1/n}-1)$$

where a value of n=1 was used whenever $n_H < 1.5$ and a value of n=2 was used when $n_H \geq 1.5$. Samples were assayed in triplicate and were typically ±5%. $K_i$ values were determined using 6 or more drug concentrations.

Compounds of the invention generally have binding affinities ($K_i$) of less than 1 μM in either Test A and or Test B.

Test C—Assay for P-glycoprotein-mediated effux

P-glycoprotein-mediated (Pgp) transport was assayed in Madin-Darby Canine Kidney Cells Expressing Human P-glycoprotein (MDR1-MDCK) cells as follows.

MDR1-MDCK cell lines were maintained in culture in Dulbecco's Minimal Essential Medium (DMEM) containing 10% Fetal Bovine Serum (FBS) at 37° C. and 5% $CO_2$ and were passaged twice weekly.

To perform the assay, cells are seeded into the apical side (A) of 12-well Costar plates at 0.5 mL per well at a cell density of 300,000 cells per mL or into 24-well Falcon plates at 0.4 mL per well at a cell density of 150,000 cells per mL and 1.5 mL (12-well plates) or 1 mL (24-well plates) of medium is added to the transwell basolateral (B) chambers. The medium is replaced daily and monolayers are used for transport assays 3 days post seeding. Monolayers are fed 2 h prior to performing a transport assay.

Chopstick electrodes are positioned to contact the medium on both sides of a monolayer and the resistance across the monolayer is determined. Normal values for the resistance across a monolayer are 130 to 160 Ohms/$cm^2$.

Transport assays are performed manually with 12-well plates and run in basolateral to apical (B to A) and apical to basolateral (A to B) directions in triplicate. Test compounds are dissolved in DMSO and diluted to the test concentrations with HBSS with the final concentration of DMSO in test solutions <1%. Transwells are washed with HBSS at 37° C. for 20 to 40 min and complement plates are prepared.

For A to B experiments, 1.5 mL of HBSS is added to the well followed by 0.5 mL test solution to the insert. For B to A experiments, 1.5 mL test solution is added to the well followed by 0.5 mL HBSS to the insert. The inserts are transferred to the complement plate and the plates incubated in a 37° C. water bath with a shaking rate of 70 rpm for 60 min. At the end of each experiment, the inserts are removed from the plates and samples transferred from both donor and receiver chambers to HPLC vials and analyzed by conventional by LC/MS/MS methods. Calibration standards of 0, 0.005, 0.05, and 0.5 μM were used. Calculation of Results:

The apparent permeability is calculated according to the following equations:

$$Papp=[(Vr \times Cr) \div (A \times t \times Co)] \times 1,000,000 \ (10^{-6} \ cm/sec)$$

$$Flux \ Ratio = Papp_{(B \ to \ A)} \div Papp_{(A \ to \ B)}$$

$$MB(\% \ Recovery) = \{[(Vr \times Cr)+(Vd \times Cd)] \div (Vd \times Co)\} \times 100$$

Where: Vr=Volume of receiver $cm^3$; Cr=Concentration in receiver at 60 min; Co=Initial concentration in donor; Vd=Volume of donor; Cd=Concentration in donor at 60 min; A=Surface area of Transwells and t=60 min.

Compounds of the invention generally have an A-B/B-A ratio of less than 2.5 in this test.

PREPARATION OF COMPOUNDS OF THE INVENTION

Compounds of the invention may be prepared according to Scheme I.

SCHEME I:

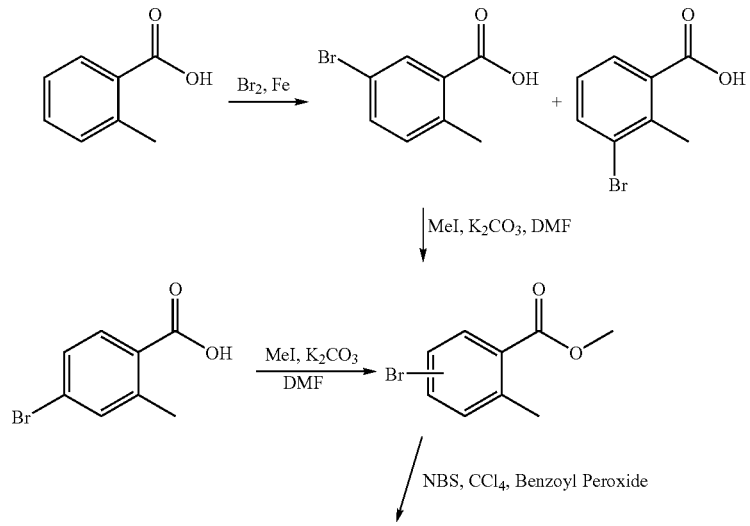

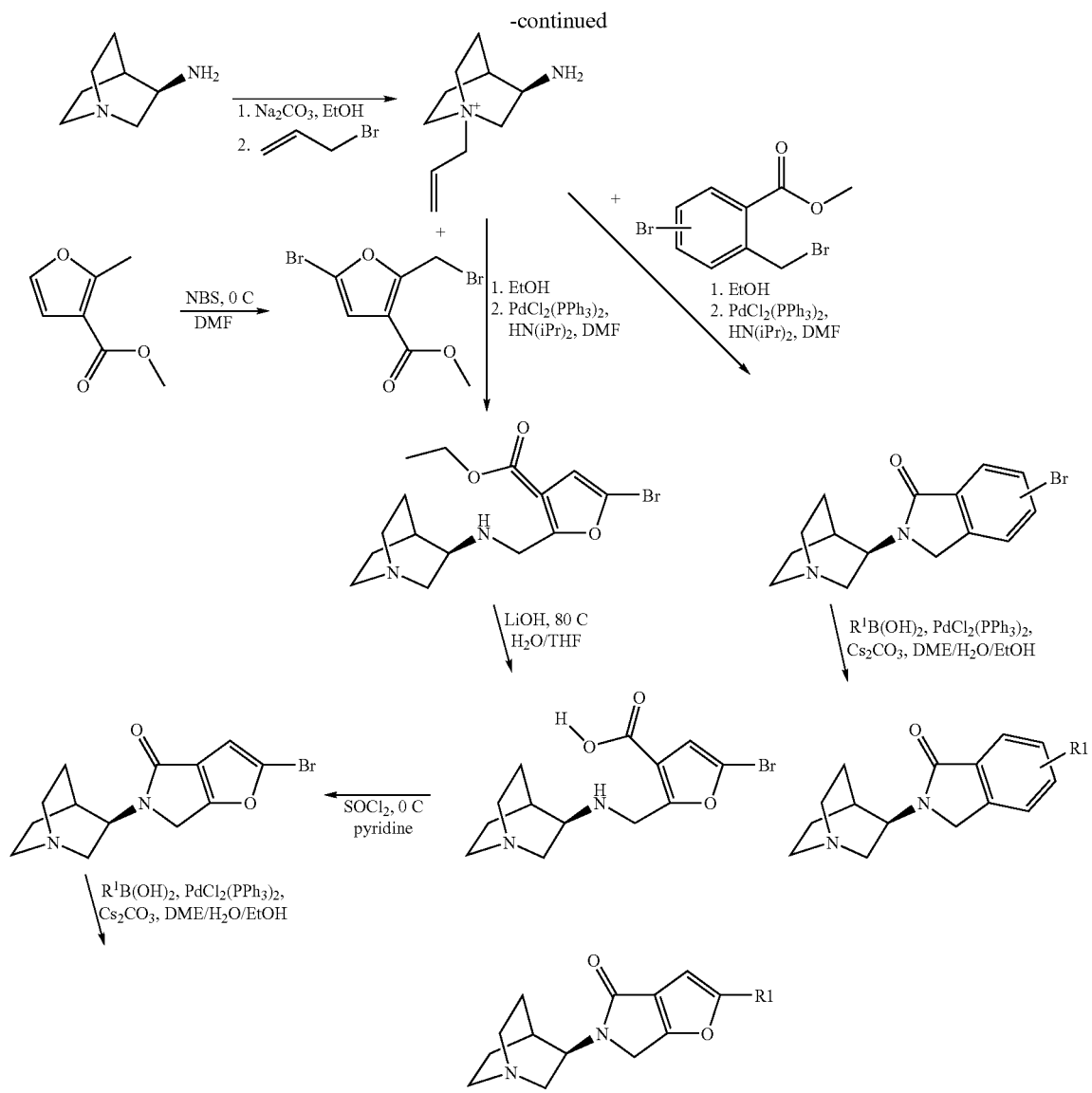

General Experimental Procedures and Definitions

Unless otherwise indicated, halo includes chloro, bromo, fluoro and iodo; $C_{1-6}$alkyl includes methyl, ethyl and linear, cyclic or branched propyl, butyl, pentyl or hexyl; $C_{2-6}$alkenyl includes ethenyl, 1-propenyl, 2-propenyl or 3-propenyl and linear, branched or cyclic butenyl, pentenyl or hexenyl; $C_{2-6}$alkynyl includes ethynyl or propynyl; the $C_{1-4}$alkyl groups referred to herein, e.g., methyl, ethyl, n-propyl, n-butyl, i-propyl, i-butyl, t-butyl, s-butyl, whether alone or part of another group, may be straight-chained or branched, and the $C_{3-4}$alkyl groups may also be cyclic, e.g., cyclopropyl or cyclobutyl. Alkyl groups referred to herein may have one, two or three halogen atom substituents thereon.

Unless otherwise indicated, aryl refers to a phenyl ring which may have 1, 2 or 3 substituents as described herein.

Unless otherwise indicated, heteroaryl refers to a 5- or 6-membered aromatic or heteroaromatic ring containing zero to three nitrogen atoms, zero or one oxygen atom, and zero or one sulfur atom, provided that the ring contains at least one nitrogen, oxygen, or sulfur atom, which may have one or more substituents as described herein.

Unless otherwise indicated, in the following examples:

(i) operations were carried out at ambient temperature, i.e., in the range 17 to 25° C. and under an atmosphere of an inert gas such as argon or nitrogen;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on ICN Ecochrom 60 Angstrom silica gel. In cases where Reverse Phase High Pressure Liquid Chromatography (RP-HPLC) was employed as a method of purification, Gilson instrumentation (215 Injector, 333 Pumps and 155 UV/Vis Detector) and a Varian C8 reverse phase column (60 Angstrom irregular load in 8 μm particle size, 41.4 mm ID×250 mm) were employed. Gradient elution was performed with aqueous 0.1% trifluoroacetic acid/acetonitrile with 0.1% trifluoroacetic acid. Sample collection was based on signal at 254 nm unless otherwise noted. In cases where Normal Phase High Pressure Liquid Chromatography (NP-HPLC) was required, Dynamax instrumentation (Dual SD-1 Pumps and UV-1 UV/Vis Detector with a Superprep Flow Cell and a Rainin silica normal phase column (60 Angstrom irregular load in 8 µm particle size, 41.4 mm ID×250 mm) were employed. Isocratic elution was performed with 0.5% isopropyl alcohol in hexanes. Supercritical Fluid Chromatography (SFC) was performed on a Berger Autoprep SFC system generally using methanol (containing 0.5% dimethyl ethyl amine) in carbon dioxide and a Berger Diol column (5 micron, 60 Å pore size).

(iv) in general, the structures of the end-products of compounds were confirmed by nuclear magnetic resonance (NMR) and/or mass spectral (MS) techniques; AP/CI mass spectral data were obtained using a Waters Platform LCZ spectrometer and, where appropriate, either positive ion data or negative ion data were collected; NMR chemical shift values were measured on the delta scale [proton magnetic resonance spectra were determined using a Bruker Avance 300 spectrometer operating at a field strength of 300 MHz; the following abbreviations have been used: s, singlet; d, doublet; t, triplet; q, quartet; m, multiplet; br, broad;

(v) structures and purity of intermediates were assessed by thin layer chromatographic, HPLC, infra-red (IR) and/or NMR analysis;

(vi) melting points were determined using a Meltemp 3.0 melting point apparatus or an oil-bath apparatus; melting points for compounds were determined after crystallization from an appropriate organic solvent or solvent mixture;

(viii) DMSO is dimethylsulphoxide.

INTERMEDIATES AND STARTING MATERIALS

The starting materials for the compounds described herein were either obtained commercially or were prepared by standard methods from known materials. For example, the following Methods illustrate, but do not limit, the preparation of intermediates and starting materials.

Method A:

2-(R)-1-Aza-bicyclo[2.2.2]oct-3-yl-6-bromo-2,3-dihydro-isoindol-1-one

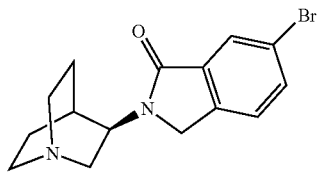

In general, the procedure of Cappelli et al., (Bioorganic & Medicinal Chemistry (2002), 10(3), 779-801.) was followed. (R)-(1-Aza-bicyclo[2.2.2]oct-3-yl)amine hydrochloride salt (1.14 g, 5.72 mmol) and sodium carbonate (2.43 g, 23 mmol) were refluxed in ethanol (60 mL) for 1 hour. The solution was cooled to 0° C. in an ice bath. The allyl bromide (657 mg, 5.43 mmol) was added and the reaction was stirred at 0° C. for 15 minutes, room temperature for 15 minutes, and finally at reflux for 30 minutes. The resulting (R)-1-allyl-1-aza-bicyclo [2.2.2]oct-3-ylamine was then directly treated with 5-bromo-2-bromomethyl-benzoic acid methyl ester (5.72 mmol) in a minimal amount of ethanol and heated at reflux overnight. The resulting mixture was filtered while still hot and the filtrate was concentrated under reduced pressure. The residue was taken up in N,N'-dimethylformamide (60 mL) and treated sequentially with palladium bistriphenylphosphine dichloride (110 mg, 0.16 mmol) and diisopropyl amine (3.6 mL, 25.7 mmol). The solution was heated at 100° C. for 1 hour. HPLC indicated complete conversion to the deprotected product. The solvent was removed under high vacuum and the resulting slurry was partitioned between 1N hydrochloride acid and chloroform (2×80 mL). After vigorous shaking, the layers were separated and the aqueous layer was extracted with chloroform (2×80 mL). The aqueous layer was adjusted to pH>12 with 5N sodium hydroxide and again extracted with chloroform (3×80 mL). The latter organic layers were combined, dried over sodium sulfate, filtered, and evaporated under reduced pressure to provide a solid. The solid was triturated in acetone/diethyl ether and filtered to afford the title compound as a tan solid (490 mg, 27%). A portion of this solid was purified for analytical purposes by reverse phase HPLC using a gradient of 20 to 60% acetonitrile in water with 0.1% trifluoroacetic acid as the eluent. The compound was obtained as a white solid (58% recovery). $^1$H NMR (300.132 MHz, DMSO) δ 7.79 (s, 1H), 7.77 (dd, J=6.6 Hz, J=1.9 Hz, 1H), 7.57 (d, J=8.8 Hz, 1H), 4.67 (q, J=18.8 Hz, 2H), 4.19 (t, J=8.1 Hz, 1H), 3.12 (ddd, J=14.1, 9.9, 2.1 Hz, 1H), 3.00-2.88 (m, 2H), 2.73 (t, J=7.7 Hz, 3H), 2.00 (q, J=2.8 Hz, 1H), 1.84-1.70 (m, 1H), 1.69-1.56 (m, 1H), 1.47-1.34 (m, 1H), 1.24 (s, 1H); MS m/z: 321/323 (M+H)$^+$.

5-Bromo-2-bromomethyl-benzoic acid methyl ester

5-Bromo-2-methyl-benzoic acid methyl ester (1.31 g, 5.72 mmol) was dissolved in carbon tetrachloride (40 mL). Benzoyl peroxide (10-20 mg) and NBS (1.01 g, 5.72 mmol) were added and the reaction mixture was heated to reflux at 100° C. The reaction course was followed by HPLC and determined to be complete after 1.25 hours. Silica gel was added and the solvent was removed under reduced pressure. The material was purified on silica gel using 5% ethyl acetate in hexanes as the eluent and was determined to be 85% pure by NMR (contained 10% starting material and 5% 5-bromo-2,2-dibromomethyl-benzoic acid methyl ester) and then used without further purification. $^1$H NMR (300.132 MHz, CDCl$_3$) δ 8.10 (d, J=2.2 Hz, 1H), 7.62 (dd, J=8.3, 2.1 Hz, 1H), 7.34 (d, J=8.5 Hz, 1H), 4.90 (s, 2H), 4.90 (s, 3H).

5-Bromo-2-methyl-benzoic acid methyl ester

A 60:40 mixture of 5-bromo-2-methyl benzoic acid and 3-bromo-2-methyl benzoic acid (8.0 g, 0.037 mol) was dissolved in N,N'-dimethylformamide (130 mL). Methyl iodide (2.28 mL, 2.3 mol) and potassium carbonate (5.11 g, 0.037 mol) were added in sequence at room temperature. The mixture was stirred at room temperature for 2 hours at which point the reaction was determined to be complete by HPLC. The solvent was removed under high vacuum and the resulting residue was passed through a silica gel column using 5% ethyl acetate in hexanes as the eluent. The mixture of isomers was obtained as an oil and then separated by preparative normal phase HPLC using 0.5% isopropyl alcohol in hexanes as the eluent. The title compound was obtained as a white solid (1.38 g, 29%). $^1$H NMR (300.132 MHz, CDCl$_3$) δ 8.04

(d, J=2.2 Hz, 1H), 7.50 (dd, J=8.2, 2.2 Hz, 1H), 7.12 (d, J=8.2 Hz, 1H), 3.89 (s, 3H), 2.54 (s, 3H).

5-Bromo-2-methyl benzoic acid

A round-bottomed flask was charged with bromine (4 mL, 78 mmol) and iron (300 mg) and cooled to 0° C. The 2-methyl benzoic acid (5.0 g, 37 mmol) was added and the slurry stirred at room temperature overnight. The mixture was carefully triturated with water to provide a reddish tan solid which was isolated by filtration and dried at 50° C. for 4 hours The material (8.0 g, quantitative) was determined by NMR to be a 60:40 mixture of the 5- and 3-bromo isomers. $^1$H NMR (300.132 MHz, CDCl$_3$) δ 8.19 (s, 1H), 7.56 (d, J=7.7 Hz, 1H), 7.16 (d, J=7.8 Hz, 1H), 2.61 (s, 3H).

Further purification was performed on a separate batch of the 60:40 mixture by taking 12.5 grams of the mixture and dissolving it in 200 mL of Methanol. While stirring at room temperature 250 mL of 0.1 N aqueous hydrochloric acid was added slowly producing a white solid. This solid was filtered and dried at 60° C. under vacuum to produce 4.31 grams of an off-white solid as the single 5-bromo toluic acid isomer. $^1$H NMR (300.132 MHz, DMSO) δ 7.91 (d, J=2.2 Hz, 1H), 7.64 (dd, J=7.9, 2.2 Hz, 1H), 7.28 (d, J=8.4 Hz, 1H), 3.17 (s, 1H), 2.47 (s, 3H).

Method B:

Method B utilizes the starting materials described in method A and the process described in Example 2.

Method C:

5-(R)-1-Aza-bicyclo[2.2.2]oct-3-yl-2-bromo-5,6-dihydro-furo[2,3-c]pyrrol-4-one

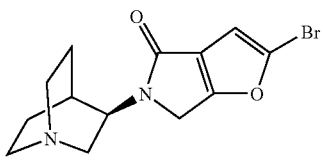

2-{[(R)-(1-Aza-bicyclo[2.2.2]oct-3-yl)amino]-methyl}-5-bromo-furan-3-carboxylic acid (3.92 mmol) was dissolved in pyridine (35 mL) and cooled to 0° C. Thionyl chloride (572 μL, 7.84 mmol) was added in one portion and the reaction was stirred at room temperature overnight. HPLC indicated starting material was still present. Additional thionyl chloride (286 μL, 3.92 mmol) was added at 0° C. After 1 hour at room temperature, HPLC indicated that all the starting material had been consumed. The reaction mixture was concentrated under reduced pressure and the resulting residue taken up in chloroform and washed with 1 N hydrochloric acid. The aqueous layer was extracted with chloroform and then basified to pH 12 with 5 N sodium hydroxide. The basic aqueous layer was then extracted with chloroform. The latter organic layers were combined, dried over sodium sulfate, filtered, and evaporated under reduced pressure to afford a brown oil. The oil was taken up in diethyl ether and evaporated twice to give a tan-brown powdery solid. The solid was washed with diethyl ether, isolated by filtration, and dried under vacuum overnight to afford the title compound as a brown solid (509 mg, 41%). $^1$H NMR (300.132 MHz, DMSO) δ 6.91 (s, 1H), 4.67 (q, J=17.1 Hz, 2H), 4.09 (t, J=7.9 Hz, 1H), 3.09 (t, J=12.1 Hz, 1H), 2.93-2.79 (m, 2H), 2.70 (t, J=7.4 Hz, 3H), 1.93 (d, J=2.5 Hz, 1H), 1.79-1.66 (m, 1H), 1.64-1.52 (m, 2H), 1.45-1.31 (m, 1H); MS m/z: 311/313 (M+H)$^+$.

2-{[(R)-(1-Aza-bicyclo[2.2.2]oct-3-yl)amino]-methyl}-5-bromo-furan-3-carboxylic acid 2-{[(R)-(1-Aza-bicyclo[2.2.2]oct-3-yl)amino]-methyl}-5-bromo-furan-3-carboxylic acid ethyl ester (1.4 g, 3.92 mmol) was dissolved in tetrahydrofuran (30 mL). A solution of lithium hydroxide (94 mg, 3.92 mmol) in water (30 mL) was added and the mixture was heated at 90° C. for 45 minutes, 50° C. for 1 hour, and then 80° C. for 0.5 hours. Additional lithium hydroxide (20 mg, 0.83 mmol) and ethanol (1 mL) were added and the reaction was heated at 80° C. for 0.5 hours and then at reflux for 15 minutes. At this point, HPLC analysis indicated the reaction had reached completion. The solvents were removed under reduced pressure. The residue was stripped from toluene (1 time) and used directly in the next reaction. MS m/z: 329/331 (M+H)$^+$.

2-{[(R)-(1-Aza-bicyclo[2.2.2]oct-3-yl)amino]-methyl}-5-bromo-furan-3-carboxylic acid ethyl ester

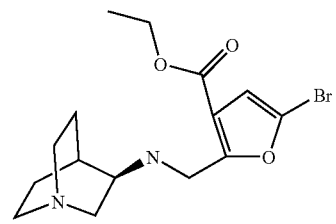

The title compound was prepared from (R)-(1-aza-bicyclo[2.2.2]oct-3-yl)amine hydrochloride salt and 5-bromo-2-bromomethyl-furan-3-carboxylic acid methyl ester according to the procedure outlined in Method A. Rather than the expected cyclization, transesterification of the methyl ester to the ethyl ester occurred. After the usual workup, a portion of the material (4.66 g, dark brown oil) was purified by reverse phase HPLC using a gradient of 10 to 30% acetonitrile in water with 0.1% trifluoroacetic acid as the eluent (2 inch C8 reverse phase column, Gilson system). The fractions were combined and concentrated to afford an oil which was taken up in 1.0 N sodium hydroxide and extracted with chloroform. The organic layers were dried over sodium sulfate, filtered, and concentrated to afford the title compound as a clear oil. The remainder of the material was purified on silica gel using 5% 7N ammonia in methanol in chloroform as eluent. The compound was obtained as a white solid. $^1$H NMR (300.132 MHz, DMSO) δ 10.81 (bs, 1H), 6.99 (s, 1H), 4.48 (bs, 2H), 4.29 (q, J=7.0 Hz, 2H), 3.76-3.05 (m, 7H), 2.31-2.17 (m, 1H), 2.03-1.71 (m, 3H), 1.31 (t, J=7.1 Hz, 3H), 1.09 (t, J=7.0 Hz, 1H); MS m/z: 357/359 (M+H)$^+$.

5-Bromo-2-bromomethyl-furan-3-carboxylic acid methyl ester

The title compound was prepared as described by Khatuya (Tetrahedron Letters (2001), 42(14), 2643-2644.). 2-Methyl-furan-3-carboxylic acid methyl ester (5.0 g, 35.7 mmol) was dissolved in N,N'-dimethylformamide (10 mL) and cooled to 0° C. N-bromosuccinimide (NBS) (15.88 g, 89.2 mmol) was added in portions. Approximately 6.5 grams of NBS were added over 45 minutes at which point it was determined by HPLC that complete formation of 5-bromo-2-methyl-furan-3-carboxylic acid methyl ester had occurred. The reaction was allowed to warm to room temperature and the remainder of the NBS was added over 1.5 hours. The reaction mixture was partitioned between diethyl ether and water. The aqueous layer was extracted with ether and the combined organic layers were dried over sodium sulfate, filtered, and evaporated under reduced pressure. The N,N'-dimethylformamide was removed under high vacuum and the material was absorbed onto silica gel and passed through a column of silica gel using 5% ethyl acetate in hexanes as the eluent. The title compound was obtained as a very pale greenish, waxy solid (4.86 g, 46%). $^1$H NMR (300.132 MHz, DMSO) δ 6.93 (s, 1H), 4.93 (s, 2H), 3.82 (s, 3H).

Method D:

Method D utilizes the starting materials described in Method A and the process described in Example 4.

Method E:

Method E utilizes as starting materials a product from Method A and the process described in Example 5.

EXAMPLES

Example 1

2-(R)-1-Aza-bicyclo[2.2.2]oct-3-yl-6-phenyl-2,3-dihydro-isoindol-1-one

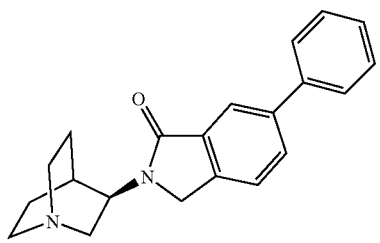

2-(R)-1-Aza-bicyclo[2.2.2]oct-3-yl-6-bromo-2,3-dihydro-isoindol-1-one (200 mg, 0.62 mmol), phenyl boronic acid (89.7 mg, 0.75 mmol), palladium bistriphenylphosphine dichloride (56 mg, 0.08 mmol), and cesium carbonate (403 mg, 1.24 mmol) were combined in a Smith microwave vial and dissolved in ethylene glycol dimethyl ether/water/ethanol (1:1:1, 3 mL). The mixture was heated in a Smith microwave at 150° C. for 10 minutes. The reaction mixture was cooled and treated with 1 N sodium hydroxide and extracted with chloroform (3 times). The organic layers were combined, dried over sodium sulfate, filtered, and evaporated under reduced pressure to afford the product as an oil. The material was purified by reverse phase HPLC using a gradient of 20 to 60% acetonitrile:water with 0.1% trifluoroacetic acid over 25 minutes. The product containing fractions were pooled and partitioned between 2 N sodium hydroxide and chloroform. The organic layers were combined, dried over sodium sulfate, filtered, and evaporated under reduced pressure to afford the title compound as a white solid (67 mg, 34%). $^1$H NMR (300.132 MHz, DMSO) δ 7.90 (dd, J=8.2 Hz, J=1.8 Hz, 1H), 7.88 (s, 1H), 7.72 (t, J=6.6 Hz, 2H), 7.70 (q, J=7.0 Hz, 1H), 7.49 (t, J=7.5 Hz, 2H), 7.40 (t, J=7.3 Hz, 1H), 4.74 (q, J=18.5 Hz, 2H), 4.24 (t, J=8.3 Hz, 1H), 3.15 (ddd, J=14.7, 10.1, 1.7 Hz, 1H), 3.04-2.90 (m, 2H), 2.75 (t, J=8.1 Hz, 3H), 2.06-1.99 (m, 1H), 1.88-1.76 (m, 1H), 1.71-1.58 (m, 2H), 1.50-1.38 (m, 1H); MS m/z: 319 (M+H)$^+$.

Example 2

2-(R)-1-Aza-bicyclo[2.2.2]oct-3-yl-5-(4-methyl-piperazin-1-yl)-2,3-dihydro-isoindol-1-one

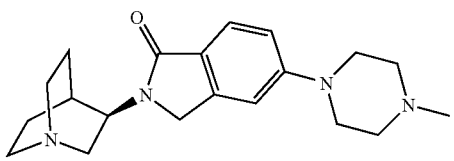

A 50 mL round-bottomed flask was charged with 2-(R)-1-aza-bicyclo[2.2.2]oct-3-yl-5-bromo-2,3-dihydro-isoindol-1-one (250 mg, 0.778 mmol), tris(dibenzylidineacetone)-dipalladium(O) (Pd$_2$(dba)$_3$) (15 mg, 0.016 mmol), 2,2'-bis(diphenylphospino)-1,1'binapthyl (BINAP) (30 mg, 0.047 mmol) and toluene (8 mL). The reaction mixture was sequentially treated with sodium t-butoxide (94 mg, 1.09 mmol) and 1-methyl piperazine (0.104 mL, 0.934 mmol). The reaction mixture was heated at 80° C. overnight. The solvent was removed under reduced pressure and the residue was suspended in 5% methanol in chloroform and filtered through a plug of diatomaceous earth. The solvent was removed under reduced pressure and the material was purified by reverse phase HPLC using a gradient of 10 to 40% acetonitrile in water with 0.1% trifluoroacetic acid as the eluent. The fractions were combined and concentrated to afford an oil which was taken up in 1.0 N sodium hydroxide and extracted with chloroform. The organic layers were dried over sodium sulfate, filtered, and concentrated to afford the title compound as a white solid (114 mg, 43%). $^1$H NMR (300.132 MHz, DMSO) δ 7.45 (d, J=8.4 Hz, 1H), 7.04 (s, 1H), 7.03 (d, J=9.1 Hz, 1H), 4.56 (q, J=18.1 Hz, 2H), 4.14 (t, J=8.0 Hz, 1H), 3.25 (t, J=5.2 Hz, 4H), 3.08 (t, J=11.8 Hz, 1H), 2.98-2.85 (m, 2H), 2.72 (t, J=7.2 Hz, 3H), 2.45 (t, J=4.8 Hz, 4H), 2.22 (s, 3H), 1.94 (t, J=3.0 Hz, 1H), 1.83-1.71 (m, 1H), 1.67-1.53 (m, 2H), 1.47-1.34 (m, 1H); MS m/z: 341 (M+H)$^+$.

Example 3

5-(R)-1-Aza-bicaclo[2.2.2]oct-3-yl-2-phenyl-5,6-dihydro-furo[2,3-c]pyrrol-4-one

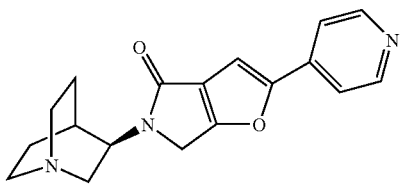

The title compound was prepared as a pale green solid in 28% yield from 5-(R)-1-aza-bicyclo[2.2.2]oct-3-yl-2-bromo-5,6-dihydro-furo[2,3-c]pyrrol-4-one and phenyl boronic acid in a manner similar to that described in Example A except that UV detection during purification was at 280 nm. $^1$H NMR (300.132 MHz, DMSO) δ 7.75 (d, J=7.6 Hz, 2H), 7.46 (t, J=7.5 Hz, 2H), 7.35 (t, J=7.2 Hz, 1H), 7.21 (s, 1H), 4.74 (q, J=17.3 Hz, 2H), 4.13 (t, J=8.1 Hz, 1H), 3.12 (ddd, J=13.4, 9.9, 1.8 Hz, 1H), 2.96-2.85 (m, 2H), 2.71 (t, J=7.3 Hz, 3H), 1.96 (q, J=2.8 Hz, 1H), 1.84-1.71 (m, 1H), 1.66-1.56 (m, 2H), 1.46-1.33 (m, 1H); MS m/z: 309 (M+H)$^+$.

Example 4

2-(R)-1-Aza-bicyclo[2.2.2]oct-3-yl-6-(4-chloro-phenyl)-2,3-dihydro-isoindol-1-one

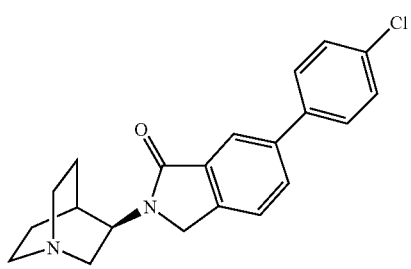

2-(R)-1-Aza-bicyclo[2.2.2]oct-3-yl-6-bromo-2,3-dihydro-isoindol-1-one (130 mg, 0.41 mmole), 4-chlorophenylboronic acid (70 mg, 0.45 mmol), palladium bistriphenylphosphine dichloride (57 mg, 0.081 mmole), and cesium carbonate (395 mg, 1.21 mmole) were dissolved in ethanol/ethylene glycol dimethyl ether/water (7:3:2 5 ml). Heated to 80° C. for 30 minutes. The mixture was cooled and the volatiles were removed under reduced pressure. The residue was taken up in 5% methanol in chloroform and filtered through a 0.2 micron frit. The solvent was removed under reduced pressure and the material was purified by reverse phase HPLC using a gradient of 10 to 40% acetonitrile in water with 0.1% trifluoroacetic acid as the eluent. The fractions were combined and concentrated to afford an oil which was taken up in 1.0 N sodium hydroxide and extracted with chloroform. The organic layers were dried over sodium sulfate, filtered, and concentrated to afford the title compound as a white solid (98 mg, 68%). $^1$H NMR (300.132 MHz, DMSO) δ 7.92-7.87 (m, 2H), 7.76 (d, J=10.2 Hz, 2H), 7.68 (d, J=11.3 Hz, 1H), 7.53 (d, J=16.2 Hz, 2H), 4.80 and 4.68 (AB, J=18.5 Hz, 2H), 4.24 (t, J=7.9 Hz, 1H), 3.14-3.08 (m, 1H), 3.06-2.91 (m, 2H), 2.76 (t, J=11.1 Hz, 1H), 2.02 (s, 1H), 1.87-1.77 (m, 2H), 1.70-1.59 (m, 2H), 1.51-1.38 (m, 2H); MS m/z: 353 (M+H)$^+$.

Example 5

N-[3-((R)-2-1-Aza-bicyclo[2.2.2]oct-3-yl-3-oxo-2,3-dihydro-1H-isoindol-5-yl)-phenyl]-butyramide

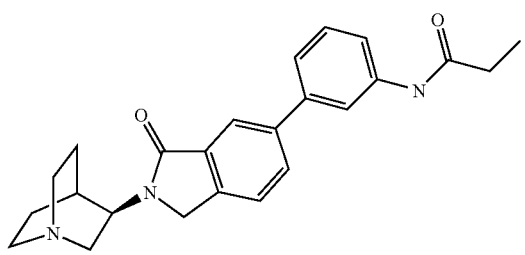

6-(3-Amino-phenyl)-2-(R)-1-aza-bicyclo[2.2.2]oct-3-yl-2,3-dihydro-isoindol-1-one (84 mg, 0.252 mmol) was dissolved in tetrahydrofuran (4 ml). To this solution was added butyryl chloride in one portion. This solution was then stirred at room temperature. The reaction course was followed by HPLC and determined to be complete after 1.5 hours. The solvent was removed under reduced pressure. The material was purified by silica gel using 5% 7N ammoniated methanol in chloroform. The compound was obtained as a tan solid (58% recovery). $^1$H NMR (300.132 MHz, DMSO) δ 9.98 (s, 1H), 8.01 (s, 1H), 7.86 (d, J=8.2 Hz, 2H), 7.83 (s, 2H), 7.69 (d, J=7.7 Hz, 1H), 7.63-7.57 (m, 2H), 7.42-7.38 (m, 2H), 4.82 and 4.69 (AB, J=18 Hz, 2H), 4.25 (t, J=7.9 Hz, 1H), 3.15 (t, J=11.6 Hz, 1H), 3.04-2.91 (m, 2H), 2.76 (t, J=9.6 Hz, 1H), 2.34 (q, J=8.6 Hz, 2H), 2.01 (s, 1H), 1.89-1.73 (m, 1H), 1.72-1.57 (m, 1H), 1.49-1.37 (m, 1H), 1.10 (t, J=10.5 Hz, 3H); MS m/z: 390 (M+H)$^+$.

Examples 6-23

Compounds of examples 6 to 23 in accord with the formula below

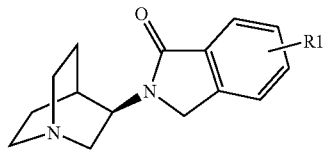

were prepared according to the procedures described herein.

Example 6

2-(R)-1-Aza-bicyclo[2.2.2]oct-3-yl-6-bromo-2,3-dihydro-isoindol-1-one

Compound obtained as a white solid, in 27% yield. (See Method A.) $^1$H NMR (300.132 MHz, DMSO) δ 7.79 (s, 1H), 7.77 (dd, J=6.6 Hz, J=1.9 Hz, 1H), 7.57 (d, J=8.8 Hz, 1H), 4.67 (q, J=18.8 Hz, 2H), 4.19 (t, J=8.1 Hz, 1 H), 3.12 (ddd, J=14.1, 9.9, 2.1 Hz, 1H), 3.00-2.88 (m, 2H), 2.73 (t, J=7.7 Hz, 3H), 2.00 (q, J=2.8 Hz, 1H), 1.84-1.70 (m, 1H), 1.69-1.56 (m, 1H), 1.47-1.34 (m, 1H), 1.24 (s, 1H); MS m/z: 321/323 (M+H)$^+$.

Example 7

2-(R)-1-Aza-bicyclo[2.2.2]oct-3-yl-6-pyridin-3-yl-2,3-dihydro-isoindol-1-one

Compound prepared as an off-white solid in 22% yield from 2-(R)-1-aza-bicyclo[2.2.2]oct-3-yl-6-bromo-2,3-dihydro-isoindol-1-one and 3-pyridyl boronic acid as described in Example 1. $^1$H NMR (300.132 MHz, DMSO) δ 8.95 (d, J=2.0 Hz, 1H), 8.60 (dd, J=4.6, 1.4 Hz, 1H), 8.15 (dt, J=8.3, 1.9 Hz, 1H), 7.96 (m, 2H), 7.72 (d, J=8.4 Hz, 1H), 7.51 (dd, J=8.1, 4.8 Hz, 1H), 4.76 (q, J=18.6 Hz, 2H), 4.24 (t, J=8.3 Hz, 1H), 3.16 (ddd, J=14.1, 10.1, 1.8 Hz, 1H), 3.06-2.89 (m, 2H), 2.75 (t, J=7.5 Hz, 3H), 2.05-2.00 (m, 1H), 1.89-1.75 (m, 1H), 1.72-1.59 (m, 2H), 1.50-1.38 (m, 1H); MS m/z: 320 (M+H)$^+$.

Example 8

2-(R)-1-Aza-bicyclo[2.2.2]oct-3-yl-6-pyridin-4-yl-2,3-dihydro-isoindol-1-one

Compound prepared as an off white solid in 23% yield from 2-(R)-1-aza-bicyclo[2.2.2]oct-3-yl-6-bromo-2,3-dihydro-isoindol-1-one and 4-pyridyl boronic acid as described Example 1. $^1$H NMR (300.132 MHz, DMSO) δ 8.66 (d, J=5.9 Hz, 2H), 8.04 (s, 1H), 8.03 (dd, J=5.9, 1.7 Hz, 1H), 7.79 (dd, J=4.5, 1.6 Hz, 1H), 7.76 (t, J=8.3 Hz, 2H), 4.77 (q, J=18.9 Hz, 2H), 4.24 (t, J=8.3 Hz, 1H), 3.15 (ddd, J=14.3, 10.1, 1.7 Hz, 1H), 3.06-2.89 (m, 2H), 2.75 (t, J=7.7 Hz, 3H), 2.03 (q, J=2.7 Hz, 1H), 1.88-1.75 (m, 1H), 1.72-1.58 (m, 2H), 1.50-1.37 (m, 1H); MS m/z: 320 (M+H)$^+$.

Example 9

2-(R)-1-Aza-bicyclo[2.2.2]oct-3-yl-5-bromo-2,3-dihydro-isoindol-1-one

Compound prepared as a white solid in 30% yield from (R)-(1-aza-bicyclo[2.2.2]oct-3-yl)amine hydrochloride salt and 4-bromo-2-bromomethyl-benzoic acid methyl ester as described in Example 1. $^1$H NMR (300.132 MHz, DMSO) δ 7.83 (s, 1H), 7.63 (q, J=10.1 Hz, 1H), 7.61 (s, 1H), 4.69 (q, J=18.7 Hz, 2H), 4.18 (t, J=7.9 Hz, 1H), 3.13 (ddd, J=14.9, 10.2, 1.6 Hz, 1H), 3.00-2.86 (m, 2H), 2.73 (t, J=7.6 Hz, 3H), 2.02-1.96 (m, 1H), 1.84-1.71 (m, 1H), 1.68-1.55 (m, 2H), 1.48-1.29 (m, 1H); MS m/z: 321/323 (M+H)+.

Example 10

2-(R)-1-Aza-bicyclo[2.2.2]oct-3-yl-5-phenyl-2,3-dihydro-isoindol-1-one

Compound prepared as a white solid in 17% yield from 2-(R)-1-aza-bicyclo[2.2.2]oct-3-yl-5-bromo-2,3-dihydro-isoindol-1-one and phenyl boronic acid as described in Example 1. $^1$H NMR (300.132 MHz, CDCl$_3$) δ 7.90 (d, J=7.7 Hz, 1H), 7.71-7.58 (m, 4H), 7.51-7.37 (m, 3H), 4.65 (dd, J=22.8, 16.6 Hz, 2H), 4.45 (t, J=8.4 Hz, 1H), 3.38 (ddd, J=14.8, 10.3, 2.0 Hz, 1H), 3.07 (dd, J=14.2, 6.9 Hz, 2H), 2.91 (t, J=7.7 Hz, 3H), 2.16 (q, J=2.9 Hz, 1H), 1.93-1.78 (m, 1H), 1.77-1.51 (m, 3H); MS m/z: 319 (M+H)$^+$.

Example 11

2-(R)-1-Aza-bicyclo[2.2.2]oct-3-yl-5-pyridin-3-yl-2,3-dihydro-isoindol-1-one Compound prepared as a white solid in 38% yield from 2-(R)-1-aza-bicyclo[2.2.2]oct-3-yl-5-bromo-2,3-dihydro-isoindol-1-one and 3-pyridyl boronic acid as described in Example 1.* $^1$H NMR (300.132 MHz, CDCl$_3$) δ 8.88 (d, J=1.9 Hz, 1H), 8.65 (dd, J=4.8, 1.4 Hz, 1H), 7.95 (d, J=7.9 Hz, 1H), 7.91 (dt, J=8.0, 2.0 Hz, 1H), 7.68 (d, J=8.3 Hz, 1H), 7.66 (s, 1H), 7.41 (dd, J=8.2, 4.9 Hz, 1H), 4.67 (dd, J=22.6, 16.8 Hz, 2H), 4.45 (t, J=8.3 Hz, 1H), 3.39 (ddd, J=15.3, 10.2, 2.2 Hz, 1H), 3.07 (dd, J=13.9, 6.6 Hz, 2H), 2.91 (t, J=7.3 Hz, 3H), 2.16 (q, J=2.9 Hz, 1H), 1.91-1.78 (m, 1H), 1.77-1.52 (m, 3H); MS m/z: 320 (M+H)$^+$.

Example 12

2-(R)-1-Aza-bicyclo[2.2.2]oct-3-yl-5-pyridin-4-yl-2,3-dihydro-isoindol-1-one Compound prepared as a tan/white residue in 17% yield from 2-(R)-1-aza-bicyclo[2.2.2]oct-3-yl-5-bromo-2,3-dihydro-isoindol-1-one and 4-pyridyl boronic acid as described in Example 1.* $^1$H NMR (300.132 MHz, CDCl$_3$) δ 8.71 (dd, J=4.4, 1.4 Hz, 2H), 7.96 (d, J=7.9 Hz, 1H), 7.73 (d, J=9.4 Hz, 1H), 7.71 (s, 1H), 7.52 (dd, J=4.4, 1.6 Hz, 2H), 4.67 (dd, J=24.4, 16.6 Hz, 2H), 4.45 (t, J=8.3 Hz, 1H), 3.39 (ddd, J=14.6, 10.1, 1.9 Hz, 1H), 3.07 (dd, J=14.7, 6.7 Hz, 2H), 2.91 (t, J=7.4 Hz, 3H), 2.16 (q, J=2.8 Hz, 1H), 1.95-1.78 (m, 2H), 1.78-1.65 (m, 1H), 1.64-1.51 (m, 1H); MS m/z: 320 (M+H)$^+$.

Example 13

2-(R)-1-Aza-bicyclo[2.2.2]oct-3-yl-4-bromo-2,3-dihydro-isoindol-1-one

Compound prepared as a light tan solid in 36% yield from (R)-(1-aza-bicyclo[2.2.2]oct-3-yl)amine hydrochloride salt and 3-bromo-2-bromomethyl-benzoic acid methyl ester as described in Example 1.** $^1$H NMR (300.132 MHz, DMSO) δ 7.86 (d, J=7.8 Hz, 1H), 7.74 (d, J=7.6 Hz, 1H), 7.49 (t, J=7.8 Hz, 1H), 4.66 (dd, J=45.8, 17.6 Hz, 2H), 4.50 (t, J=8.5 Hz, 1H), 3.65 (d, J=8.6 Hz, 2H), 3.50-3.11 (m, 4H), 2.45-2.40 (m, 1H), 2.34-2.28 (m, 1H), 2.21-2.04 (m, 2H), 2.01-1.70 (m, 1H); MS m/z: 321/323 (M+H)$^+$.

Example 14

2-(R)-1-Aza-bicyclo[2.2.2]oct-3-yl-4-phenyl-2,3-dihydro-isoindol-1-one

Compound prepared as a white solid in 33% yield from 2-(R)-1-aza-bicyclo[2.2.2]oct-3-yl-4-bromo-2,3-dihydro-isoindol-1-one and phenyl boronic acid as described in Example 1. $^1$H NMR (300.132 MHz, CDCl$_3$) δ 7.89-7.82 (m, 1H), 7.57-7.42 (m, 7H), 4.61 (dd, J=27.0, 17.0 Hz, 2H), 4.40 (t, J=8.3 Hz, 1H), 3.35 (ddd, J=14.6, 10.0, 2.0 Hz, 1H), 3.10-2.95 (m, 2H), 2.88 (t, J=7.5 Hz, 3H), 2.13 (q, J=2.8 Hz, 1H), 1.86-1.64 (m, 3H), 1.55-1.45 (m, 1H); MS m/z: 319 (M+H)$^+$.

Example 15

2-(R)-1-Aza-bicyclo[2.2.2]oct-3-yl-4-pyridin-3-yl-2,3-dihydro-isoindol-1-one Compound prepared as a white foam in 17% yield from 2-(R)-1-aza-bicyclo[2.2.2]oct-3-yl-4-bromo-2,3-dihydro-isoindol-1-one and 3-pyridyl boronic acid as described in Example 1. $^1$H NMR (300.132 MHz, CDCl$_3$) δ 8.77 (s, 1H), 8.69 (d, J=4.1 Hz, 1H), 7.91 (dd, J=7.3, 0.9 Hz, 1H), 7.80 (dt, J=7.9, 1.8 Hz, 1H), 7.61 (t, J=7.5 Hz, 1H), 7.55 (dd, J=7.6, 1.0 Hz, 1H), 7.46 (dd, J=8.1, 4.9 Hz, 1H), 4.61 (dd, J=24.4, 16.9 Hz, 2H), 4.40 (t, J=8.3 Hz, 1H), 3.36 (ddd, J=14.1, 10.1, 1.9 Hz, 1H), 3.09-2.95 (m, 2H), 2.94-2.81 (m, 3H), 2.13 (q, J=2.9 Hz, 1H), 1.87-1.47 (m, 4H); MS m/z: 320 (M+H)$^+$.

Example 16

2-(R)-1-Aza-bicyclo[2.2.2]oct-3-yl-4-pyridin-4-yl-2,3-dihydro-isoindol-1-one Compound prepared as a light tan solid in 20% yield from 2-(R)-1-aza-bicyclo[2.2.2]oct-3-yl-4-bromo-2,3-dihydro-isoindol-1-one and 4-pyridyl boronic acid as described in Example 1. $^1$H NMR (300.132 MHz, CDCl$_3$) δ 8.75 (dd, J=4.3, 1.6 Hz, 2H), 7.93 (dd, J=6.5, 2.1 Hz, 1H), 7.61 (q, J=6.7 Hz, 1H), 7.59 (t, J=6.4 Hz, 1H), 7.40 (dd, J=4.4, 1.6 Hz, 2H), 4.63 (dd, J=27.0, 17.0 Hz, 2H), 4.40 (t, J=8.4 Hz, 1H), 3.37 (ddd, J=13.9, 9.9, 2.1 Hz, 1H), 3.10-2.96 (m, 2H), 2.95-2.82 (m, 3H), 2.13 (q, J=2.9 Hz, 1H), 1.87-1.47 (m, 4H); MS m/z: 320 (M+H)⁺.

Example 17

2-(R)-1-Aza-bicyclo[2.2.2]oct-3-yl-7-bromo-2,3-dihydro-isoindol-1-one

Compound prepared as an off white solid in 54% yield from (R)-(1-aza-bicyclo[2.2.2]oct-3-yl)amine hydrochloride salt and 2-bromo-6-bromomethyl-benzoic acid methyl ester as described in Example 1.** ¹H NMR (300.132 MHz, DMSO) δ 7.63 (dd, J=17.1, 7.7 Hz, 2H), 7.51 (t, J=7.6 Hz, 1H), 4.67 (q, J=18.2 Hz, 2H), 4.37 (t, J=8.0 Hz, 1H), 3.50 (t, J=11.7 Hz, 1H), 3.36 (dd, J=13.6, 6.8 Hz, 1H), 3.26 (td, J=11.8, 4.8 Hz, 1H), 3.09 (t, J=7.7 Hz, 3H), 2.26 (q, J=3.1 Hz, 1H), 2.06-1.94 (m, 1H), 1.90-1.79 (m, 2H), 1.69 (t, J=12.2 Hz, 1H); MS m/z: 321/323 (M+H)⁺.

** Material of Examples 13 and 17 obtained as an oil was taken up in diethyl ether/chloroform and treated with excess 1.0 M hydrochloric acid in diethyl ether to form a solid. The solid was isolated by filtration and then converted to the free base by washing in 2 N sodium hydroxide and chloroform. The organic layers were dried over sodium sulfate, filtered, and concentrated to provide the desired compound as a solid.

Example 18

2-(R)-1-Aza-bicyclo[2.2.2]oct-3-yl-7-phenol-2,3-dihydro-isoindol-1-one

Compound prepared as pale yellow solid in 26% yield from 2-(R)-1-aza-bicyclo[2.2.2]oct-3-yl-7-bromo-2,3-dihydro-isoindol-1-one and phenyl boronic acid as described in Example 1. ¹H NMR (300.132 MHz, CDCl₃) δ 7.57 (t, J=7.2 Hz, 1H), 7.56-7.50 (m, 2H), 7.47-7.36 (m, 5H), 4.61 (dd, J=22.2, 16.6 Hz, 2H), 4.40 (t, J=8.3 Hz, 1H), 3.33 (ddd, J=14.5, 10.3, 2.3 Hz, 1H), 3.05-2.80 (m, 5H), 2.11 (q, J=2.8 Hz, 1H), 1.89-1.71 (m, 3H), 1.70-1.60 (m, 1H); MS m/z: 319 (M+H)⁺.

Example 19

2-(R)-1-Aza-bicyclo[2.2.2]oct-3-yl-7-pyridin-3-yl-2,3-dihydro-isoindol-1-one

Compound prepared as a pale yellow solid in 22% yield from 2-(R)-1-aza-bicyclo[2.2.2]oct-3-yl-7-bromo-2,3-dihydro-isoindol-1-one and 3-pyridyl boronic acid as described in Example 1. ¹H NMR (300.132 MHz, CDCl₃) δ 8.72 (d, J=2.0 Hz, 1H), 8.62 (dd, J=4.8, 1.5 Hz, 1H), 7.95 (dt, J=7.8, 1.9 Hz, 1H), 7.62 (t, J=7.6 Hz, 1H), 7.51 (d, J=7.6 Hz, 1H), 7.39 (d, J=7.8 Hz, 1H), 7.35 (dd, J=7.7, 5.0 Hz, 1H), 4.63 (dd, J=23.8, 16.8 Hz, 2H), 4.39 (t, J=8.1 Hz, 1H), 3.34 (ddd, J=14.3, 9.9, 2.2 Hz, 1H), 3.07-2.77 (m, 5H), 2.11 (q, J=2.8 Hz, 1H), 1.89-1.48 (m, 4H); MS m/z: 320 (M+H)⁺.

Example 20

2-(R)-1-Aza-bicyclo[2.2.2]oct-3-yl-7-pyridin-4-yl-2,3-dihydro-isoindol-1-one

Compound prepared as an off white solid in 96% yield from 2-(R)-1-aza-bicyclo[2.2.2]oct-3-yl-7-bromo-2,3-dihydro-isoindol-1-one and 4-pyridyl boronic acid as described in Example 1. ¹H NMR (300.132 MHz, CDCl₃) δ 8.67 (dd, J=4.6, 1.6 Hz, 2H), 7.62 (t, J=7.5 Hz, 1H), 7.53 (d, J=7.4 Hz, 1H), 7.47 (dd, J=4.6, 1.5 Hz, 2H), 7.38 (d, J=7.6 Hz, 1H), 4.64 (dd, J=23.6, 17.0 Hz, 2H), 4.39 (t, J=8.2 Hz, 1H), 3.34 (ddd, J=14.3, 10.3, 2.0 Hz, 1H), 3.09-2.78 (m, 5H), 2.11 (q, J=2.8 Hz, 1H), 1.90-1.63 (m, 3H), 1.63-1.49 (m, 1H); MS m/z: 320 (M+H)⁺.

Example 21

(R)-2-(1-Aza-bicyclo[2.2.2]oct-3-yl)-2,3-dihydro-isoindol-1-one

Compound prepared as a light tan solid in 4% yield from (R)-(1-aza-bicyclo[2.2.2]oct-3-yl)amine hydrochloride salt and 2-bromo-methyl-benzoic acid methyl ester as described in Example 1.* ¹H NMR (300.132 MHz, CDCl₃) δ 7.85 (d, J=7.5 Hz, 1H), 7.58-7.41 (m, 3H), 4.59 (dd, J=23.8, 16.5 Hz, 3H), 4.43 (t, J=8.1 Hz, 1H), 3.36 (ddd, J=14.1, 10.0, 2.1 Hz, 1H), 3.05 (q, J=7.0 Hz, 2H), 2.90 (t, J=7.6 Hz, 3H), 2.13 (q, J=2.8 Hz, 1H), 1.91-1.76 (m, 2H), 1.75-1.64 (m, 1H), 1.61-1.49 (m, 1H); MS m/z: 243 (M+H)⁺.

* The compounds of Examples 11, 12 and 21 were purified by preparative SFC using 38% methanol (containing 0.5% dimethyl ethyl amine) in carbon dioxide and a Berger Diol column (5 micron, 60 Å pore size).

Example 22

2-(R)-1-Aza-bicyclo[2.2.2]oct-3-yl-5-(4-methyl-piperazin-1-yl)-2,3dihydro-isoindol-1-one Compound obtained as a white solid in 43% yield. (See Example 2.) ¹H NMR (300.132 MHz, DMSO) δ 7.45 (d, J=8.4 Hz, 1H), 7.04 (s, 1H), 7.03 (d, J=9.1 Hz, 1H), 4.56 (q, J=18.1 Hz, 2H), 4.14 (t, J=8.0 Hz, 1H), 3.25 (t, J=5.2 Hz, 4H), 3.08 (t, J=11.8 Hz, 1H), 2.98-2.85 (m, 2H), 2.72 (t, J=7.2 Hz, 3H), 2.45 (t, J=4.8 Hz, 4H), 2.22 (s, 3H), 1.94 (t, J=3.0 Hz, 1H), 1.83-1.71 (m, 1H), 1.67-1.53 (m, 2H), 1.47-1.34 (m, 1H); MS m/z: 341 (M+H)⁺.

Example 23

2-(R)-1-Aza-bicyclo[2.2.2]oct-3-yl-5-morpholin-4-yl-2,3-dihydro-isoindol-1-one

Compound prepared as a white solid in 23% yield from 2-(R)-1-aza-bicyclo[2.2.2]oct-3-yl-5-bromo-2,3-dihydro-isoindol-1-one and morpholine in a fashion similar to that described for Example 2. ¹H NMR (300.132 MHz, DMSO) δ 7.48 (d, J=8.1 Hz, 1H), 7.06 (s, 1H), 7.04 (dd, J=9.4, 2.0 Hz, 1H), 4.57 (q, J=18.3 Hz, 2H), 4.15 (t, J=8.0 Hz, 1H), 3.75 (t, J=4.8 Hz, 4H), 3.22 (t, J=4.8 Hz, 4H), 3.09 (ddd, J=13.9, 10.1, 1.8 Hz, 1H), 2.94 (dd, J=14.2, 6.7 Hz, 2H), 2.72 (t, J=7.6 Hz, 3H), 1.96 (q, J=2.7 Hz, 1H), 1.84-1.71 (m, 1H), 1.62 (dd, J=8.6, 2.9 Hz, 2H), 1.48-1.35 (m, 1H); MS m/z: 328 (M+H)⁺.

Examples 24-27

Compounds of examples 24 to 27 in accord with the formula below

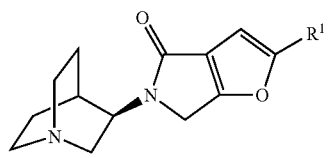

were prepared according to the procedures described herein.

Example 24

5-(R)-1-Aza-bicyclo[2.2.2]oct-3-yl-2-bromo-5,6-dihydro-furo[2,3-c]pyrrol-4-one

Compound obtained as a brown solid in 41% yield. (See Method B.) $^1$H NMR (300.132 MHz, DMSO) δ 6.91 (s, 1H), 4.67 (q, J=17.1 Hz, 2H), 4.09 (t, J=7.9 Hz, 1H), 3.09 (t, J=12.1 Hz, 1H), 2.93-2.79 (m, 2H), 2.70 (t, J=7.4 Hz, 3H), 1.93 (d, J=2.5 Hz, 1H), 1.79-1.66 (m, 1H), 1.64-1.52 (m, 2H), 1.45-1.31 (m, 1H); MS m/z: 311/313 (M+H)$^+$.

Example 25

5-(R)-1-Aza-bicyclo[2.2.2]oct-3-yl-2-phenyl-5,6-dihydro-furo[2,3-c]pyrrol-4-one

Compound obtained as a pale green solid in 28% yield. (See Example 3.) $^1$H NMR (300.132 MHz, DMSO) δ 7.75 (d, J=7.6 Hz, 2H), 7.46 (t, J=7.5 Hz, 2H), 7.35 (t, J=7.2 Hz, 1H), 7.21 (s, 1H), 4.74 (q, J=17.3 Hz, 2H), 4.13 (t, J=8.1 Hz, 1H), 3.12 (ddd, J=13.4, 9.9, 1.8 Hz, 1H), 2.96-2.85 (m, 2H), 2.71 (t, J=7.3 Hz, 3H), 1.96 (q, J=2.8 Hz, 1H), 1.84-1.71 (m, 1H), 1.66-1.56 (m, 2H), 1.46-1.33 (m, 1H); MS m/z: 309 (M+H)$^+$.

Example 26

5-(R)-1-Aza-bicyclo[2.2.2]oct-3-yl-2-pyridin-3-yl-5,6-dihydro-furo[2,3-c]pyrrol-4-one

Compound prepared as a white solid in 30% yield from 5-(R)-1-aza-bicyclo[2.2.2]oct-3-yl-2-bromo-5,6-dihydro-furo[2,3-c]pyrrol-4-one and 3-(5,5-dimethyl-[1,3,2]dioxaborinan-2-yl)-pyridine in a fashion similar to that described for Example 3. $^1$H NMR (300.132 MHz, DMSO) δ 9.00 (d, J=2.0 Hz, 1H), 8.54 (dd, J=4.9, 1.6 Hz, 1H), 8.12 (dt, J=8.0, 1.9 Hz, 1H), 7.49 (dd, J=8.1, 4.8 Hz, 1H), 7.38 (s, 1H), 4.76 (q, J=17.3 Hz, 2H), 4.14 (t, J=7.3 Hz, 1H), 3.12 (ddd, J=14.8, 12.1, 3.3 Hz, 1H), 2.90 (dd, J=12.5, 6.3 Hz, 2H), 2.71 (t, J=6.6 Hz, 3H), 1.97 (q, J=2.7 Hz, 1H), 1.85-1.71 (m, 1H), 1.66-1.57 (m, 2H), 1.47-1.33 (m, 1H); MS m/z: 310 (M+H)$^+$.

Example 27

5-(R)-1-Aza-bicyclo[2.2.2]oct-3-yl-2-pyridin-4-yl-5,6-dihydro-furo[2,3-c]pyrrol-4-one

Compound prepared as a white solid in 21% yield from 5-(R)-1-aza-bicyclo[2.2.2]oct-3-yl-2-bromo-5,6-dihydro-furo[2,3-c]pyrrol-4-one and 4-pyridyl boronic acid in a fashion similar to that described for Example 3. $^1$H NMR (300.132 MHz, DMSO) δ 8.63 (dd, J=4.5, 1.4 Hz, 2H), 7.70 (dd, J=4.7, 1.4 Hz, 2H), 7.56 (s, 1H), 4.78 (q, J=17.6 Hz, 2H), 4.14 (t, J=7.6 Hz, 1H), 3.12 (ddd, J=13.2, 9.8, 1.7 Hz, 1H), 2.90 (dd, J=14.2, 6.7 Hz, 2H), 2.72 (t, J=7.1 Hz, 3H), 1.97 (q, J=2.7 Hz, 1H), 1.84-1.71 (m, 1H), 1.61 (septet, J=3.7 Hz, 2H), 1.47-1.33 (m, 1H); MS m/z: 310 (M+H)$^+$.

Other compounds of the invention are:
- 2-(R)-1-Aza-bicyclo[2.2.2]oct-3-yl-6-(3-chloro-phenyl)-2,3-dihydro-isoindol-1-one;
- 2-(R)-1-Aza-bicyclo[2.2.2]oct-3-yl-6-(4-chloro-phenyl)-2,3-dihydro-isoindol-1-one;
- 2-(R)-1-Aza-bicyclo[2.2.2]oct-3-yl-6-quinolin-8-yl-2,3-dihydro-isoindol-1-one;
- 2-(R)-1-Aza-bicyclo[2.2.2]oct-3-yl-6-benzo[1,3]dioxol-5-yl-2,3-dihydro-isoindol-1-one;
- 2-(R)-1-Aza-bicyclo[2.2.2]oct-3-yl-6-(2-chloro-phenyl)-2,3-dihydro-isoindol-1-one;
- 2-(R)-1-Aza-bicyclo[2.2.2]oct-3-yl-6-(2-methoxy-phenyl)-2,3-dihydro-isoindol-1-one;
- N-[3-((R)-2-1-Aza-bicyclo[2.2.2]oct-3-yl-3-oxo-2,3-dihydro-1H-isoindol-5-yl)-phenyl]-acetamide;
- 2-(R)-1-Aza-bicyclo[2.2.2]oct-3-yl-6-morpholin-4-yl-2,3-dihydro-isoindol-1-one, and
- 4-((R)-2-1-Aza-bicyclo[2.2.2]oct-3-yl-3-oxo-2,3-dihydro-1H-isoindol-5-yl)-N,N-dimethyl-benzamide.

Examples 28-72

Compounds shown in the following table in accord with the following formula were synthesized in a fashion analogous to the above examples.

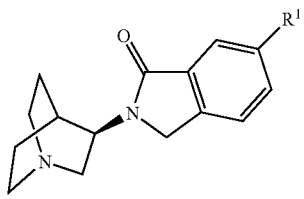

| Ex. | R$^1$ | Chemical Name | Experimental Data | α7 Ki |
|---|---|---|---|---|
| 28 | 6-(4-methoxy-phenyl) | 2-(R)-1-Aza-bicyclo[2.2.2]oct-3-yl-6-(4-methoxy-phenyl)-2,3-dihydro-isoindol-1-one | Title compound obtained as a tan solid in 21% yield (see Method A for details). $^1$H NMR (300.132 MHz, DMSO) δ7.86-7.81 (m, 2H), 7.69-7.61 (m, 3H), 7.04 (d,J=15.1 Hz, 2H), 4.78 and 4.65(AB, J =17.8 Hz, 2H), 4.23 (t, J= 10.4 Hz, 1H), 3.81 (s, 3H), 3.22-3.09 (m, 1H), 3.05-2.89 (m, 1H), 2.79-2.70 (m, 2H), 2.02 (s, 2H), 1.83-1.74 (m, 1H), 1.69-1.54 (m, 2H), | 7.7E-08 |

-continued

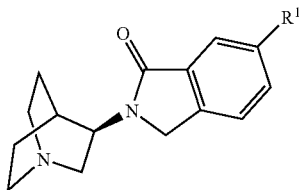

| Ex. | R[1] | Chemical Name | Experimental Data | α7 Ki |
|---|---|---|---|---|
| | | | 1.52-1.34 (m, 2H), 1.50-1.37 (m, 2H); MS m/z 349 (M+H)+. | |
| 29 | 6-chloro | 2-(R)-1-Aza-bicyclo[2.2.2]oct-3-yl-6-chloro-2,3-dihydro-isoindol-1-one | Title compound obtained as a white solid in 32% yield (see Method A starting materials for details). $^1$H NMR (300.132 MHz, DMSO) δ7.67-7.60 (m, 3H), 4.75 and 4.63 (AB, J =18.0 Hz Hz, 2H), 4.19 (t, J= 9.9 Hz, 1H), 3.18-3.07 (m, 1H), 3.01-2.86 (m, 2H), 2.73 (t, J=8.3 Hz, 2H), 2.03 (s, 1H), 1.84-1.70 (m, 2H), 1.70-1.56 (m, 2H), 1.46-1.35 (m, 1H); MS m/z: 277 (M+H)+. | 2.89E-07 |
| 30 | 6-(3-methoxy-phenyl) | 2-(R)-1-Aza-bicyclo[2.2.2]oct-3-yl-6-(3-methoxy-phenyl)-2,3-dihydro-isoindol-1-one | Title compound obtained as a tan solid in 34% yield (see Method A for details). $^1$H NMR (300.132 MHz, DMSO) δ7.92-7.87 (m, 2H), 7.69-7.65 (m, 1H), 7.40 (t, J =9.3 Hz, 1H), 7.26 (t, J=12.3 Hz, 2H), 6.99-6.94 (m, 1H), 4.80 and 4.68 (AB, J=18.0 Hz, 2H), 4.24 (t, J=9.2 Hz, 1H), 3.84 (s, 3H),3.21-3.08 (m, 1H), 3.06-2.91 (m, 1H), 2.80-2.70 (m, 2H), 2.04-1.99 (m, 1H), 1.88-1.74 (m, 2H), 1.73-1.59 (m, 2H), 1.51-1.36 (m, 2H); MS m/z 349 (M+H)+. | 2.18E-08 |
| 31 | 6-(3-chloro-phenyl) | 2-(R)-1-Aza-bicyclo[2.2.2]oct-3-yl-6-(3-chloro-phenyl)-2,3-dihydro-isoindol-1-one | Title compound obtained as a tan solid in 15% yield (see Method A for details). $^1$H NMR (300.132 MHz, DMSO) δ7.95-7.90 (m, 2H), 7.79 (s, 1H), 7.70 (t, J=7.3 Hz, 2H), 7.55-7.44 (m, 2H), 4.81 and 4.68 (AB, J=18.5 Hz, 2H), 4.24 (t, J=8.8 Hz, 1H), 3.22-3.11 (m, 1H), 3.05-2.91 (m, 1H), 2.81-2.71 (m, 2H), 2.05-1.98 (m, 1H), 1.88-1.75 (m, 2H), 1.71-1.57 (m, 2H), 1.51-1.37 (m, 2H); MS m/z: 353 (M+H)+. | 4.54E-08 |
| 32 | 6-(4-chloro-phenyl) | 2-(R)-1-Aza-bicyclo[2.2.2]oct-3-yl-6-(4-chloro-phenyl)-2,3-dihydro-isoindol-1-one | Title compound obtained as a white solid in 68% yield (see Method D for details). $^1$H NMR (300.132 MHz, DMSO) δ7.92-7.87 (m, 2H), 7.76 (d, J= 10.2 Hz, 2H), 7.68 (d, J =11.3 Hz, 1H), 7.53 (d, J=16.2 Hz, 2H), 4.80 and 4.68 (AB, J= 18.5 Hz, 2H), 4.24 (t, J=7.9 Hz, 1H), 3.14-3.08 (m, 1H), 3.06-2.91 (m, 2H), 2.76 (t, J =11.1 Hz, 1H), 2.02 (s, 1H), 1.87-1.77 (m, 2H), 1.70-1.59 (m, 2H), 1.51-1.38 (m, 2H); MS m/z: 353 (M+H)+. | 9.0E-08 |
| 33 | 6-quinolin-8-yl | 2-(R)-1-Aza-bicyclo[2.2.2]oct-3-yl-6-quinolin-8- | Title compound obtained as a white solid in 64% yield (see Method D for details). $^1$H | 9.0E-08 |

-continued

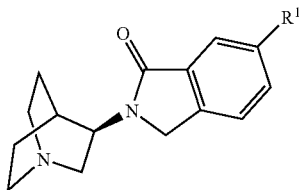

| Ex. | R[1] | Chemical Name | Experimental Data | α7 Ki |
|---|---|---|---|---|
| | | yl-2,3-dihydro-isoindol-1-one | NMR (300.132 MHz, DMSO) δ8.90 (s, 1H), 8.44 (d, J= 22.6 Hz, 1H), 8.02 (d, J =22.8 Hz, 1H), 7.92-7.76 (m, 2H), 7.73-7.62 (m, 2H), 7.61-7.53 (m, 2H), 4.83 and 4.71 (AB, J=18.0 Hz, 2H), 4.29-4.20 (m, 1H), 3.20-3.08 (m, 1H), 3.08-2.92 (m, 2H), 2.79-2.67 (m, 1H), 2.05 (s, 1H), 1.89-1.75 (m, 2H), 1.73-1.56 (m, 2H), 1.51-1.36 (m, 2H); MS m/z: 370 (M+H)+. | |
| 34 | 6-benzo[1,3]dioxol-5-yl | 2-(R)-1-Aza-bicyclo[2.2.2]oct-3-yl-6-benzo[1,3]dioxol-5-yl-2,3-dihydro-isoindol-1-one | Title compound obtained as a white solid in 63% yield (see Method D for details). $^1$H NMR (300.132 MHz, DMSO) δ7.85-7.76 (m, 2H), 7.62 (d, J=14.4 Hz, 1H), 7.30 (s, 1H), 7.19 (d, J=12.4 Hz, 1H), 7.00 (d, J=13.0 Hz, 1H), 6.07 (s, 2H), 4.77 and 4.65 (q, J=18.4 Hz, 2H), 4.25-4.19 (m, 1H), 3.19-3.05 (m, 1H), 3.05-2.87 (m, 1H), 2.82-2.64 (m, 2H), 2.01 (s, 1H), 1.87-1.72 (m, 2H),1.72-1.56(m, 2H), 1.50-1.34 (m, 2H); MS m/z: 363 (M+H)+. | 3.7E-08 |
| 35 | 6-(2-chloro-phenyl) | 2-(R)-1-Aza-bicyclo[2.2.2]oct-3-yl-6-(2-chloro-phenyl)-2,3-dihydro-isoindol-1-one | Title compound obtained as a tan solid in 50% yield (see Method D for details). $^1$H NMR (300.132 MHz, DMSO) δ7.71-7.56 (m, 4H), 7.47-7.42 (m, 3H), 4.82 and 4.70 (AB, J=18.0 Hz, 2H), 4.23 (t, J=9.5 Hz, 1H), 3.28-3.19 (m, 1H),3.18-3.08(m, 1H), 3.04-2.89 (m, 1H), 2.78-2.69 (m, 1H), 2.02 (s, 1H), 1.93-1.74 (m, 2H), 1.72-1.60 (m, 2H), 1.51-1.36 (m, 2H); MS m/z: 353 (M+H)+. | 6.3E-09 |
| 36 | 6-(2-methoxy-phenyl) | 2-(R)-1-Aza-bicyclo[2.2.2]oct-3-yl-6-(2-methoxy-phenyl)-2,3-dihydro-isoindol-1-one | Title compound obtained as a white solid in 76% yield (see Method D for details). $^1$H NMR (300.132 MHz, DMSO) δ7.72-7.59 (m, 3H), 7.41-7.29 (m, 2H), 7.14 (d, J=11.3 Hz, 1H), 7.05 (t, J=8.9 Hz, 1H), 4.78 and 4.66 (AB, J= 18.0 Hz, 2H), 4.22 (t, J=11.5 Hz, 1H), 3.77 (s, 1H), 3.28-3.23 (m, 2H), 3.14 (t, J=16.2 Hz, 2H), 3.03-2.92 (m, 1H), 2.74 (t, J=10.8 Hz, 1H), 2.01 (s, 1H), 1.86-1.77 (m, 2H), 1.70-1.59 (m, 2H), 1.50-1.36 (m, 2H); MS m/z: 349 (M+H)+. | 2.4E-08 |
| 37 | 6-(3-N-Phenyl-acetamide) | N-[3-((R)-2-1-Aza-bicyclo[2.2.2]oct-3-yl-3-oxo-2,3-dihydro-1H-isoindol-5-yl)- | Title compound obtained as a white solid in 72% yield (see Method D for details). $^1$H NMR (300.132 MHz, DMSO) δ7.97 (s, 1H), 7.84 (d, J= 13.2 Hz, 2H), 7.68 (d, J=11.4 | 70E-09 |

-continued

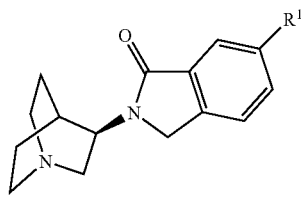

| Ex. | R¹ | Chemical Name | Experimental Data | α7 Ki |
|---|---|---|---|---|
| | | phenyl]-acetamide | Hz, 1H), 7.62-7.55 (m, 1H), 7.41-7.36 (m, 2H), 4.80 and 4.68 (AB, J=18.0 Hz, 2H), 4.24 (t, J=9.1 Hz, 1H), 3.21-3.10 (m, 1H), 3.06-2.90 (m, 2H), 2.75 (t, J=7.6 Hz, 2H), 2.07 (s, 3H), 2.04-2.00 (m, 1H), 1.88-1.75 (m, 2H), 1.69-1.60(m, 2H), 1.50-1.38(m, 2H); MS m/z 341 (M+H)+. | |
| 38 | 6-(4-methyl-piperazin-1-yl) | 2-(R)-1-Aza-bicyclo[2.2.2]oct-3-yl-6-(4-methyl-piperazin-1-yl)-2,3-dihydro-isoindol-1-one | Title compound obtained as a off white solid in 16% yield (see Method B for details). ¹H NMR (300.132 MHz, DMSO) δ7.40 (d, J=8.3 Hz, 1H), 7.22 (d, J=8.3 Hz, 1H), 7.10 (s, 1H), 4.62 and 5.50 (AB, J=18.0 Hz, 2H), 4.19 (t, J=7.8 Hz, 1H), 3.17 (s, 3H), 3.12-3.05 (m, 1H), 2.99-2.88 (m, 2H), 2.74 (t, J=7.4 Hz, 2H), 2.49-2.42 (m, 4H), 2.24 (s, 4H), 1.98 (s, 1H), 1.84-1.70 (m, 2H), 1.68-1.58 (m, 2H), 1.49-1.34 (m, 2H); MS m/z: 341 (M+H)+. | 4.24E-07 |
| 39 | 6-morpholin-4-yl | 2-(R)-1-Aza-bicyclo[2.2.2]oct-3-yl-6-morpholin-4-yl-2,3-dihydro-isoindol-1-one | Title compound obtained as a off white solid in 32% yield (see Method B for details). ¹H NMR (300.132 MHz, DMSO) δ7.43 (d, J=10.4 Hz, 1H), 7.12 (d, J=3.5 Hz, 1H), 7.23 (dd, J=2.5, 8.5 Hz, 1H), 4.62 and 5.50 (AB, J=18.0 Hz, 2H), 4.19 (t,J=8.1 Hz, 1H), 3.75 (t, J=4.8 Hz, 4H), 3.14 (t, J=4.8 Hz, 4H), 3.09-3.06 (m, 1H), 3.00-2.87 (m, 2H), 2.74 (t, J=9.3 Hz, 2H), 2.02-1.94 (m, 1H), 1.85-1.70 (m, 2H), 1.70-1.57 (m, 2H), 1.49-1.36 (m, 2H); MS m/z: 327 (M+H)+. | 4.21E-07 |
| 40 | 6-(4-N,N-dimethyl-benzamide | 4-((R)-2-1-Aza-bicyclo[2.2.2]oct-3-yl-3-oxo-2,3-dihydro-1H-isoindol-5-yl)-N,N-dimethyl-benzamide | Title compound obtained as a white solid in 62% yield (see Method D for details). ¹H NMR (300.132 MHz, DMSO) δ7.94 (d, J=8.0 Hz, 2H), 7.79 (d, J=8.0 Hz, 2H), 7.70 (d, J=7.7 Hz, 1H), 7.51 (d, J=7.8 Hz, 2H), 4.82 and 4.68 (q, J=18.0 Hz, 2H), 4.24 (t, J=7.8 Hz, 1H), 3.22-3.10 (m, 1H), 3.06-2.91 (m, 8H), 2.75 (t, J=7.4 Hz, 2H), 2.08 (s, 1H), 1.91-1.74 (m, 2H), 1.71-1.59 (m, 2H), 1.51-1.37 (m, 2H); MS m/z: 390 (M+H)+. | 3.53E-07 |
| 41 | 6-quinolin-6-yl | 2-(R)-1-Aza-bicyclo[2.2.2]oct-3-yl-6-quinolin-6-yl-2,3-dihydro-isoindol-1-one | Title compound obtained as a tan solid in 37% yield (see Method D for details). ¹H NMR (300.132 MHz, DMSO) δ8.92 (dd, J=4.3, 1.6 Hz, 1H), 8.49-8.44 (m, 1H), 8.41-8.39 (m, 2H), 8.19-8.05 (m, 3H), 7.75 (d, J=8.4 Hz, 1H), | 3.29E-07 |

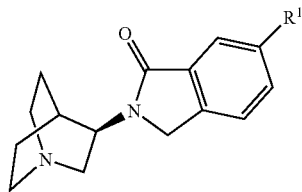

| Ex. | R¹ | Chemical Name | Experimental Data | α7 Ki |
|---|---|---|---|---|
| | | | 7.58 (dd, J=8.3, 4.2 Hz, 1H), 4.84 and 4.72 (q, J=18.0 Hz, 2H), 4.27 (t, J=8.0 Hz, 1H), 3.17 (t, J=12.8 Hz, 1H), 3.06-2.93 (m, 2H), 2.76 (t, J=7.6 Hz, 2H), 2.05 (s, 1H), 1.91-1.75 (m, 2H), 1.72-1.60 (m, 2H), 1.52-1.38 (m, 2H); MS m/z: 370 (M+H)+. | |
| 42 | 6-quinolin-5-yl | 2-(R)-1-Aza-bicyclo[2.2.2]oct-3-yl-6-quinolin-5-yl-2,3-dihydro-isoindol-1-one | Title compound obtained as a tan solid in 39% yield (see Method D for details). ¹H NMR (300.132 MHz, DMSO) δ8.92 (dd, J=4.3, 1.6 Hz, 1H), 8.49-8.44 (m, 1H), 8.41-8.39 (m, 2H), 8.19-8.05 (m, 3H), 7.75 (d, J=8.4 Hz, 1H), 7.58 (dd, J=8.3, 4.2 Hz, 1H), 4.87 and 4.83 and 4.71 (AB, J=18.0 Hz, 2H), 4.27 (t, J=8.0 Hz, 1H), 3.17 (t, J=12.8 Hz, 1H), 3.06-2.93 (m, 2H), 2.76 (t, J=7.6 Hz, 2H), 2.05 (s, 1H), 1.91-1.75 (m, 2H), 1.72-1.60 (m, 2H), 1.52-1.38 (m, 2H); MS m/z: 370 (M+H)+. | 8.96E-08 |
| 43 | 6-(3-methanesulfonyl-phenyl) | 2-(R)-1-Aza-bicyclo[2.2.2]oct-3-yl-6-(3-methanesulfonyl-phenyl)-2,3-dihydro-isoindol-1-one | Title compound obtained as a tan solid in 63% yield (see Method D for details). ¹H NMR (300.132 MHz, DMSO) δ8.24 (s, 1H), 8.11 (d, J=7.9 Hz, 1H), 8.04-7.93 (m, 3H), 7.79-7.72 (m, 2H), 4.83 and 4.71 (AB, J=18.0 Hz, 2H), 4.26 (t, J=8.1 Hz, 1H), 4.28 (s, 1H), 3.32 (s, 3H), 3.22-3.11 (m, 1H), 3.05-2.90 (m, 1H), 2.75 (t, J=8.9 Hz, 1H), 2.03 (s, 1H), 1.88-1.75 (m, 2H), 1.70-1.60 (m, 2H), 1.51-1.37 (m, 2H); MS m/z: 397 (M+H)+. | 9.4E-08 |
| 44 | 6-(4-methanesulfonyl-phenyl) | 2-(R)-1-Aza-bicyclo[2.2.2]oct-3-yl-6-(4-methanesulfonyl-phenyl)-2,3-dihydro-isoindol-1-one | Title compound obtained as a tan solid in 50% yield (see Method D for details). ¹H NMR (300.132 MHz, DMSO) δ8.03-7.97 (m, 6H), 7.76-7.72 (m, 1H), 4.83 and 4.71 (AB, J=18.0 Hz, 2H), 4.24 (t, J=8.6 Hz, 1H), 3.26 (s, 3H), 3.22-3.10 (m, 1H), 3.05-2.90 (m, 2H), 2.75 (t, J=7.5 Hz, 1H), 2.03 (s, 1H), 1.88-1.75 (m, 2H), 1.72-1.59 (m, 2H), 1.51-1.37 (m, 2H); Ms m/z: 397 (M+H)+. | 3.21E-07 |
| 45 | 6-quinolin-3-yl | 2-(R)-1-Aza-bicyclo[2.2.2]oct-3-yl-6-quinolin-3-yl-2,3-dihydro-isoindol-1-one | Title compound obtained as a tan solid in 18% yield (see Method D for details). ¹H NMR (300.132 MHz, DMSO) δ8.03-7.97 (m, 6H), 7.76-7.72 (m, 1H), 4.88 and 4.77 (AB, J=18.0 Hz, 2H), 4.24 (t, J=8.6 Hz, 1H), 3.26 (s, 3H), 3.22-3.10 (m, 1H), 3.05-2.90 (m, 2H), 2.75 (t, J=7.5 | 6.68E-08 |

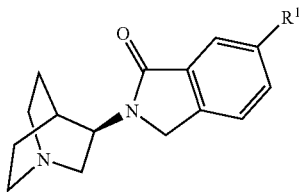

| Ex. | R¹ | Chemical Name | Experimental Data | α7 Ki |
|---|---|---|---|---|
| | | | Hz, 1H), 2.03 (s, 1H), 1.88-1.75 (m, 2H), 1.72-1.59 (m, 2H), 1.51-1.37 (m, 2H); MS m/z: 370 (M+H)+. | |
| 46 | 6-(6-methoxy-pyridin-3-yl) | 2-(R)-1-Aza-bicyclo[2.2.2]oct-3-yl-6-(6-methoxy-pyridin-3-yl)-2,3-dihydro-isoindol-1-one | Title compound obtained as a tan solid in 26% yield (see Method D for details). ¹H NMR (300.132 MHz, DMSO) δ8.54 (d, J=2.2 Hz, 1H), 8.09 (dd, J=2.6, 8.6 Hz, 1H), 7.90-7.87 (m, 2H), 7.69-7.66 (m, 1H), 6.92 (d, J=8.6 Hz, 1H), 4.79 and 4.68 (AB, J=18.0 Hz, 2H), 4.24 (t, J=8.1 Hz, 1H), 3.91 (s, 3H), 3.21-3.11 (m, 1H), 3.06-2.90 (m, 2H), 2.76 (t, J=7.9 Hz, 2H), 2.05 (s, 1H), 1.87-1.75 (m, 1H), 1.70-1.59 (m, 2H), 1.51-1.38 (m, 2H); MS m/z: 350 (M+H)+. | 2.90E-07 |
| 47 | 6-isoquinolin-5-yl | 2-(R)-1-Aza-bicyclo[2.2.2]oct-3-yl-6-isoquinolin-5-yl-2,3-dihydro-isoindol-1-one | Title compound obtained as a tan solid in 35% yield (see Method D for details). ¹H NMR (300.132 MHz, DMSO) δ9.42 (s, 1H), 8.51 (d, J=5.8 Hz, 1H), 8.21 (t, J=4.6 Hz, 1H), 7.81-7.70 (m, 6H), 7.62 (d, J=6.5 Hz, 1H), 4.87 and 4.77 (AB, J=18.0 Hz, 2H), 4.27 (t, J=7.8 Hz, 1H), 3.27-3.11 (m, 1H), 3.10-2.97 (m, 2H), 2.78 (t, J=7.5 Hz, 1H), 2.09-2.03 (m, 1H), 1.93-1.78 (m, 1H), 1.73-1.61 (m, 2H), 1.54-1.40 (m, 2H); MS m/z: 370 (M+H)+. | 3.2E-08 |
| 48 | 6-isoquinolin-4-yl | 2-(R)-1-Aza-bicyclo[2.2.2]oct-3-yl-6-isoquinolin-4-yl-2,3-dihydro-isoindol-1-one | Title compound obtained as a tan solid in 29% yield (see Method D for details). ¹H NMR (300.132 MHz, DMSO) δ9.38 (s, 1H), 8.48 (s, 1H), 8.25 (d, J=7.7 Hz, 1H), 7.81-7.75 (m, 7H), 4.88 and 4.77 (AB, J=18.0 Hz, 2H), 4.27 (t, J=7.8 Hz, 1H), 3.18 (t, J=12.2 Hz, 1H), 3.09-2.93 (m, 2H), 2.77 (t, J=7.5 Hz, 1H), 2.06 (s, 1H), 1.93-1.79 (m, 1H), 1.71-1.61 (m, 2H), 1.52-1.40 (m, 2H); MS m/z: 370 (M+H)+. | 1.12E-07 |
| 49 | 6-(4-N-Phenyl-acetamide) | N-[4-((R)-2-1-Aza-bicyclo[2.2.2]oct-3-yl-3-oxo-2,3-dihydro-1H-isoindol-5-yl)-phenyl]-acetamide | Title compound obtained as a tan solid in 24% yield (see Method D for details). ¹H NMR (300.132 MHz, DMSO) δ10.02 (s, 1H), 7.89-7.84 (m, 2H), 7.71-7.63 (m, 6H), 4.78 and 4.67 (AB, J=18.0 Hz, 2H), 4.24 (t, J=8.0 Hz, 1H), 4.06 (s, 1H), 3.21-3.14 (m, 2H), 3.05-2.91 (m, 2H), 2.76 (t, J=7.8 Hz, 1H), 2.07 (s, 1H), 2.03 (s, 1H), 1.89-1.75 (m, 1H), 1.71-1.60 (m, | 3.2E-09 |

-continued

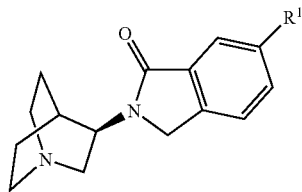

| Ex. | R[1] | Chemical Name | Experimental Data | α7 Ki |
|---|---|---|---|---|
| 50 | 6-(1-methyl-1H-pyrazol-4-yl) | 2-(R)-1-Aza-bicyclo[2.2.2]oct-3-yl-6-(1-methyl-1H-pyrazol-4-yl)-2,3-dihydro-isoindol-1-one | 2H), 1.51-1.38 (m, 2H); MS m/z: 376 (M+H)+. Title compound obtained as a tan solid in 53% yield (see Method D for details). $^1$H NMR (300.132 MHz, DMSO) δ8.25 (s, 1H), 7.94 (s, 1H), 7.83-7.76 (m, 2H), 7.55 (d, J=7.8 Hz, 1H), 4. (AB, J=18.0 Hz, 2H), 4.22 (t, J=8.1 Hz, 1H), 3.87 (s, 3H), 3.13 (t, J=11.8 Hz, 1H), 3.01-2.89 (m, 2H), 2.74 (t, J=7.6 Hz, 2H), 2.01 (s, 1H), 1.85-1.72 (m, 1H), 1.71-1.58 (m, 2H), 1.49-1.37 (m, 2H); MS m/z: 323 (M+H)+. | 6.1E-08 |
| 51 | 6-(1-benzyl-1H-pyrazol-4-yl) | 2-(R)-1-Aza-bicyclo[2.2.2]oct-3-yl-6-(1-benzyl-1H-pyrazol-4-yl)-2,3-dihydro-isoindol-1-one | Title compound obtained as a tan solid in 48% yield (see Method D for details). $^1$H NMR (300.132 MHz, DMSO) δ8.42 (s, 1H), 8.42 (s, 1H), 7.85-7.78 (m, 2H), 7.55 (d, J=7.9 Hz, 1H), 7.38-7.28 (m, 5H), 5.34 (s, 2H), 4.73 and 4.62 (AB, J=18.0 Hz, 2H), 4.22 (t, J=8.0 Hz, 1H), 3.13 (t, J=11.9 Hz, 1H), 3.02-2.88 (m, 2H), 2.74 (t, J=7.6 Hz, 2H), 2.00 (s, 1H), 1.86-1.73 (m, 1H), 1.70-1.57 (m, 2H), 1.49-1.36 (m, 2H); MS m/z: 399 (M+H)+. | 1.46E-07 |
| 52 | 6-(3-N,N-dimethyl-benzamide) | 3-((R)-2-1-Aza-bicyclo[2.2.2]oct-3-yl-3-oxo-2,3-dihydro-1H-isoindol-5-yl)-N,N-dimethyl-benzamide | Title compound obtained as a white solid in 77% yield (see Method D for details). $^1$H NMR (300.132 MHz, DMSO) δ7.95-7.89 (m, 2H), 7.80 (d, J=7.9 Hz, 1H), 7.73-7.67 (m, 2H), 7.55 (t, J=7.6 Hz, 1H), 7.41 (d, J=7.7 Hz, 1H), 4.80 and 4.70 (AB, J=18.0 Hz, 2H), 4.25 (t, J=6.4 Hz, 1H), 3.23-3.09 (m, 1H), 3.09-2.90 (m, 8H), 2.84-2.69 (m, 2H), 2.04 (s, 1H), 1.89-1.75 (m, 1H), 1.74-1.54 (m, 3H), 1.51-1.37 (m, 1H); MS m/z: 390 (M+H)+. | 3.1E-08 |
| 53 | 6-(4-N-ethyl-benzainide) | 4-((R)-2-1-Aza-bicyclo[2.2.2]oct-3-yl-3-oxo-2,3-dihydro-1H-isoindol-5-yl)-N-ethyl-benzamide | Title compound obtained as a tan solid in 52% yield (see Method D for details). $^1$H NMR (300.132 MHz, DMSO) δ8.51 (t, J=5.3 Hz, 1H), 7.98-7.92 (m, 5H), 7.83 (d, J=8.0 Hz, 2H), 7.70 (d, J=8.5 Hz, 1H), 4.81 and 4.71 (AB, J=18.0 Hz, 2H), 4.25 (t, J=7.1 Hz, 1H), 3.36-3.22 (m, 2H), 3.23-3.10 (m, 1H), 3.05-2.91 (m, 2H), 2.76 (t, J=10.5 Hz, 1H), 2.03 (s, 1H), 1.89-1.74 (m, 2H), 1.69-1.59 (m, 2H), 1.51-1.39 (m, 1H), 1.15 (t, J=7.6 Hz, 3H); MS m/z: 390 (M+H)+. | 3.48E-07 |

-continued

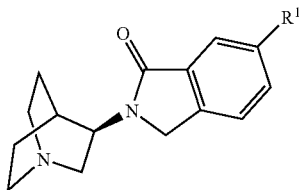

| Ex. | R¹ | Chemical Name | Experimental Data | α7 Ki |
|---|---|---|---|---|
| 54 | 6-(3,5-dimethoxy-phenyl) | 2-(R)-1-Aza-bicyclo[2.2.2]oct-3-yl-6-(3,5-dimethoxy-phenyl)-2,3-dihydro-isoindol-1-one | Title compound obtained as a white solid in 64% yield (see Method D for details). ¹H NMR (300.132 MHz, DMSO) δ8.51 (t, J=5.3 Hz, 1H), 7.98-7.92 (m, 5H), 7.83 (d, J=8.0 Hz, 2H), 7.70 (d, J=8.5 Hz, 1H), 4.79 and 4.68 (AB, J=18.0 Hz, 2H), 4.25 (t, J=7.1 Hz, 1H), 3.36-3.22 (m, 2H), 3.23-3.10 (m, 1H), 3.05-2.91 (m, 2H), 2.76 (t, J=10.5 Hz, 1H), 2.03 (s, 1H), 1.89-1.74 (m, 2H), 1.69-1.59 (m, 2H), 1.51-1.39 (m, 1H), 1.15 (t, J=7.6 Hz, 3H); MS m/z: 379 (M+H)+. | 6.69E-07 |
| 55 | 6-(3-benzamide) | 3-((R)-2-1-Aza-bicyclo[2.2.2]oct-3-yl-3-oxo-2,3-dihydro-1H-isoindol-5-yl)-benzamide | Title compound obtained as a tan solid in 46% yield (see Method D for details). ¹H NMR (300.132 MHz, DMSO) δ8.24 (s, 1H), 8.17 (s, 1H), 8.04-7.86 (m, 5H), 7.70 (d, J=8.1 Hz, 1H), 7.57 (t, J=7.7 Hz, 1H), 7.41 (s, 1H), 4.82 and 4.70 (AB, J=18.0 Hz, 2H), 4.26 (t, J=7.9 Hz, 1H), 3.17 (t, J=12.4 Hz, 1H), 3.06-2.91 (m, 1H), 2.76 (t, J=6.9 Hz, 1H), 2.07-2.00 (m, 1H), 1.89-1.74 (m, 2H), 1.72-1.59 (m, 2H), 1.52-1.37 (m, 2H); MS m/z: 362 (M+H)+. | 1.7E-08 |
| 56 | 6-(4-N-benzyl-benzamide) | 4-((R)-2-1-Aza-bicyclo[2.2.2]oct-3-yl-3-oxo-2,3-dihydro-1H-isoindol-5-yl)-N-benzyl-benzamide | Title compound obtained as a tan solid in 13% yield (see Method D for details). ¹H NMR (300.132 MHz, DMSO) δ9.10 (t, J=5.9 Hz, 1H), 8.04-7.94 (m, 3H), 7.86 (d, J=8.2 Hz, 2H), 7.71 (d, J=8.4 Hz, 1H), 7.37-7.22 (m, 5H), 4.82 and 4.69 (AB, J=18.0 Hz, 2H), 4.51 (d, J=5.9 Hz, 2H), 4.28-4.22 (m, 1H), 3.23-3.10 (m, 1H), 3.06-2.91 (m, 2H), 2.81-2.72 (m, 2H), 2.07-1.99 (m, 1H), 1.88-1.73 (m, 1H), 1.73-1.59 (m, 2H), 1.52-1.37(m, 2H);MS m/z: 452 (M+H)+. | 1.0E-07 |
| 57 | 6-(3-amino-phenyl) | 6-(3-Amino-phenyl)-2-(R)-1-aza-bicyclo[2.2.2]oct-3-yl-2,3-dihydro-isoindol-1-one | Title compound obtained as a white solid in 98% yield (see Method D for details). ¹H NMR (300.132 MHz, DMSO) δ7.82-7.76 (m, 2H), 7.64 (d, J=7.7 Hz, 1H), 7.12 (t, J=7.7 Hz, 1H), 6.91 (s, 1H), 6.83 (d, J=7.7 Hz, 1H), 6.59 (d, J=7.8 Hz, 1H), 5.22-5.18 (m, 2H), 4.79 and 4.68 (AB, J=18.0 Hz, 2H), 4.23 (t, J=10.6 Hz, 1H), 3.19-3.09 (m, 1H), 3.02-2.89 (m, 2H), 2.74 (t, J=7.5 Hz, 2H), 2.04-1.97 (m, 1H), 1.87-1.75 (m, 1H), 1.69 | 6.4E-09 |

-continued

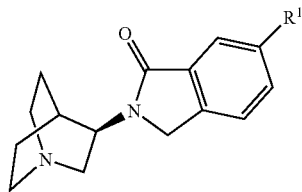

| Ex. | R[1] | Chemical Name | Experimental Data | α7 Ki |
|---|---|---|---|---|
| 58 | 6-(3-N-Phenyl-propionamide) | N-[3-((R)-2-1-Aza-bicyclo[2.2.2]oct-3-yl-3-oxo-2,3-dihydro-1H-isoindol-5-yl)-phenyl]-propionamide | -1.59 (m, 2H), 1.48-1.37 (m, 2H); MS m/z: 334 (M+H)+. Title compound obtained as a white solid in 77% yield (see Method E for details). $^1$H NMR (300.132 MHz, DMSO) δ9.98 (s, 1H), 8.01 (s, 1H), 7.88-7.82 (m, 2H), 7.69 (d, J =8.7 Hz, 1H), 7.62-7.58 (m, 1H), 7.42-7.38 (m, 2H), 4.81 and 4.68 (AB, J=18.8 Hz, 2H), 4.25 (t, J=8.3 Hz, 1H), 3.21-3.10 (m, 2H), 3.04-2.90 (m, 3H), 2.75 (t, J=7.7 Hz, 1H), 2.35 (q, J=7.3 Hz, 2H), 2.04-2.00 (m, 1H), 1.88-1.75 (m, 1H), 1.72-1.59 (m, 2H), 1.49-1.39 (m, 2H), 1.11 (t, J=7.5 Hz, 3H); MS m/z: 390 (M+H)+. | 1.7E-09 |
| 59 | 6-(5-methoxy-pyridin-3-yl) | 2-(R)-1-Aza-bicyclo[2.2.2]oct-3-yl-6-(5-methoxy-pyridin-3-yl)-2,3-dihydro-isoindol-1-one | Title compound obtained as a tan solid in 26% yield (see Method D for details). $^1$H NMR (300.132 MHz, DMSO) δ8.53 (d, J=1.4 Hz, 1H), 8.31 (d, J=2.5 Hz, 1H), 8.01-7.96 (m, 2H), 7.73-7.68 (m, 2H), 4.82 and 4.70 (AB, J=18.0 Hz, 2H), 4.24 (t, J=8.1 Hz, 1H), 3.93 (s, 3H), 3.15 (t, J= 17.0 Hz, 2H), 3.04-2.90 (m, 2H), 2.76 (t, J =7.5 Hz, 2H), 2.04-2.00 (m, 1H), 1.89-1.74 (m, 1H), 1.73-1.60 (m, 2H), 1.50-1.37 (m, 1H); MS m/z: 350 (M+H)+. | 3.83E-07 |
| 60 | 6-(2,3-dihydro-benzo[1,4]diox in-6-yl) | 2-(R)-1-Aza-bicyclo[2.2.2]oct-3-yl-6-(2,3-dihydro-benzo[1,4]dioxin-6-yl)-2,3-dihydro-isoindol-1-one | Title compound obtained as a tan solid in 88% yield (see Method D for details). $^1$H NMR (300.132 MHz, DMSO) δ7.83-7.77 (m, 2H), 7.62 (d, J=8.0 Hz, 1H), 7.20-7.16 (m, 2H), 6.95 (d, J=8.4 Hz, 1H), 4.77 and 4.66 (AB, J= 18.0 Hz, 2H), 4.30-4.19 (m, 5H), 3.22-3.08 (m, 1H), 3.05-2.89 (m, 2H), 2.75 (t, J=7.2 Hz, 2H), 2.04-1.99 (m, 1H), 1.87-1.75 (m, 1H), 1.70-1.60 (m, 2H), 1.50-1.36 (m, 2H); MS m/z: 377 (M+H)+. | 2.8E-08 |
| 61 | 6-(3-isopropoxy-phenyl) | 2-(R)-1-Aza-bicyclo[2.2.2]oct-3-yl-6-(3-isopropoxy-phenyl)-2,3-dihydro-isoindol-1-one | Title compound obtained as a white solid in 90% yield (see Method D for details). $^1$H NMR (300.132 MHz, DMSO) δ7.90-7.85 (m, 2H), 7.66 (d, J=8.1 Hz, 1H), 7.38 (t, J= 7.3 Hz, 1H), 7.25-7.19 (m, 2H), 6.96-6.92 (m, 1H), 4.84-4.63 (m, 3H), 4.24 (t, J=8.1 Hz, 1H), 3.15 (t, J=12.0 Hz, 1H), 3.05-2.90 (m, 2H), 2.76 (t, J=9.6 Hz, 2H), 2.05-2.00 (m, 1H), 1.88-1.75 (m, 1H), 1.69-1.61 (m, 2H), 1.51-1.38 (m, 1H), 1.30 (d, J=6.1 | 1.4E-08 |

-continued

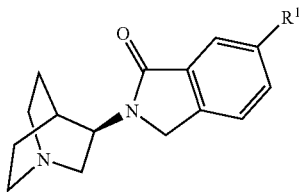

| Ex. | R¹ | Chemical Name | Experimental Data | α7 Ki |
|---|---|---|---|---|
| | | | Hz, 6H); MS m/z: 377 (M+H)+. | |
| 62 | 6-(3-trifluoromethoxy-phenyl) | 2-(R)-1-Azabicyclo[2.2.2]oct-3-yl-6-(3-trifluoromethoxy-phenyl)-2,3-dihydro-isoindol-1-one | Title compound obtained as a white solid in 78% yield (see Method D for details). ¹H NMR (300.132 MHz, DMSO) δ7.96-7.92 (m, 2H), 7.79 (d, J=7.6 Hz, 1H), 7.73-7.68 (m, 2H), 7.62 (t, J=8.2 Hz, 1H), 7.40 (d, J=8.2 Hz, 1H), 4.81 and 4.70 (AB, J=18.0 Hz, 2H), 4.24 (t, J=8.3 Hz, 1H), 3.15 (t, J=13.0 Hz, 1H), 3.06-2.90 (m, 2H), 2.75 (t, J =7.6 Hz, 2H), 2.06-2.00 (m, 1H), 1.89-1.75 (m, 1H), 1.71-1.58 (m, 1H), 1.49-1.39 (m, 2H); MS m/z: 403 (M+H)+. | 4.8E-08 |
| 63 | 6-(3-N-Phenyl-butyramide) | N-[3-((R)-2-1-Azabicyclo[2.2.2]oct-3-yl-3-oxo-2,3-dihydro-1H-isoindol-5-yl)-phenyl]-butyramide | Title compound obtained as a tan solid in 59% yield (see Method D for details). ¹H NMR (300.132 MHz, DMSO) δ9.94 (s, 1H), 8.01 (s, 1H), 7.87-7.82 (m, 2H), 7.68 (d, J =7.8 Hz, 1H), 7.63-7.58 (m, 1H), 7.42-7.37 (m, 2H), 4.80 and 4.69 (AB, J=18.0 Hz, 2H), 4.25 (t, J=7.2 Hz, 1H), 3.17 (t, J=11.5 Hz, 1H), 3.06-2.90 (m, 2H), 2.76 (t, J=6.1 Hz, 2H), 2.31 (t, J=7.3 Hz, 2H), 2.05-2.01 (m, 1H), 1.90-1.76 (m, 1H), 1.71-1.58 (m, 5H), 1.51-1.40 (m, 1H), 0.93 (t, J=7.4 Hz, 3H); MS m/z: 404 (M+H)+. | 4.5E-09 |
| 64 | 6-(3-N-Phenyl-benzamide) | N-[3-((R)-2-1-Azabicyclo[2.2.2]oct-3-yl-3-oxo-2,3-dihydro-1H-isoindol-5-yl)-phenyl]-benzamide | Title compound obtained as a tan solid in 53% yield (see Method D for details). ¹H NMR (300.132 MHz, DMSO) δ10.32 (s, 1H), 8.19 (s, 1H), 8.00 (d, J=7.0 Hz, 2H), 7.93-7.86 (m, 3H), 7.70 (d, J=8.4 Hz, 1H), 7.63-7.45 (m, 5H), 4.81 and 4.66 (AB, J=18.0 Hz, 3H), 4.26 (t, J=8.1 Hz, 1H), 3.16 (t, J=11.6 Hz, 1H), 3.06-2.91 (m, 2H), 2.76 (t, J =6.9 Hz, 2H), 2.06-2.02 (m, 1H), 1.90-1.74 (m, 2H), 1.72-1.60 (m; 2H), 1.50-1.39 (m, 1H); MS m/z: 438 (M+H)+. | 3.9E-09 |
| 65 | 6-(2-N-Phenyl-acetamide) | N-[2-((R)-2-1-Azabicyclo[2.2.2]oct-3-yl-3-oxo-2,3-dihydro-1H-isoindol-5-yl)-phenyl]-acetamide | Title compound obtained as a tan solid in 34% yield (see Method D for details). ¹H NMR (300.132 MHz, DMSO) δ9.28 (s, 1H), 7.66-7.54 (m, 3H), 7.47-7.28 (m, 4H), 4.80 and 4.68 (AB, J=18.3 Hz, 2H), 4.24 (t, J=7.6 Hz, 1H), 3.15 (t, J=13.2 Hz, 1H), 3.04-2.93 (m, 2H), 2.76 (t, J=9.5 Hz, 2H), 2.04-1.99 (m, 1H), 1.89-1.74 (m, 5H), 1.74-1.57 (m, 2H), 1.52-1.38 (m, 2H); MS m/z: 376 (M+H)+. | 1.15E-06 |

-continued

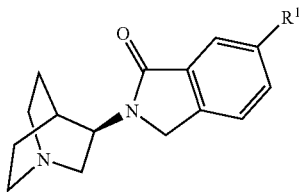

| Ex. | R¹ | Chemical Name | Experimental Data | α7 Ki |
|---|---|---|---|---|
| 66 | 6-(3-N,N-diethyl-benzamide | 3-((R)-2-1-Aza-bicyclo[2.2.2]oct-3-yl-3-oxo-2,3-dihydro-1H-isoindol-5-yl)-N,N-diethyl-benzamide | Title compound obtained as a tan solid in 65% yield (see Method D for details). ¹H NMR (300.132 MHz, DMSO) δ7.95-7.89 (m, 2H), 7.79 (d, J=7.9 Hz, 1H), 7.71-7.64 (m, 2H), 7.55 (t, J=7.6 Hz, 1H), 7.36 (d, J=9.1 Hz, 1H), 4.80 and 4.68 (AB, J=18.0 Hz, 3H), 4.24 (t, J=8.7 Hz, 1H), 3.55-3.09 (m, 5H), 3.05-2.89 (m, 2H), 2.75 (t, J=7.5 Hz, 1H), 2.05-2.00 (m, 1H), 1.88-1.75 (m, 2H), 1.70-1.60 (m, 2H), 1.49-1.39 (m, 2H), 1.22-1.02 (m, 6H). | 2.0E-08 |
| 67 | 6-(3-benzyloxy-phenyl) | 2-(R)-1-Aza-bicyclo[2.2.2]oct-3-yl-6-(3-benzyloxy-phenyl)-2,3-dihydro-isoindol-1-one | Title compound obtained as a tan solid in 32% yield (see Method D for details). ¹H NMR (300.132 MHz, DMSO) δ7.91-7.86 (m, 2H), 7.67 (d, J=8.4 Hz, 1H), 7.49 (d, J=8.4 Hz, 2H), 7.44-7.27 (m, 6H), 7.04 (dd, J=2.1, 8.1 Hz, 1H), 5.22 (s, 2H), 4.79 and 4.68 (AB, J=18.0 Hz, 2H), 4.24 (t, J=6.2 Hz, 1H), 3.16 (t, J=11.5 Hz, 1H), 3.06-2.90 (m, 2H), 2.75 (t, J=8.3 Hz, 2H), 2.05-2.01 (m, 1H), 1.87-1.74 (m, 2H), 1.71-1.60 (m, 2H), 1.51-1.39 (m, 2H); MS m/z: 425 (M+H)+. | 5.1E-08 |
| 68 | 6-[3-(morpholine-4-carbonyl)-phenyl] | 2-(R)-1-Aza-bicyclo[2.2.2]oct-3-yl-6-[3-(morpholine-4-carbonyl)-phenyl]-2,3-dihydro-isoindol-1-one | Title compound obtained as a tan solid in 63% yield (see Method D for details). ¹H NMR (300.132 MHz, DMSO) δ7.91-7.86 (m, 2H), 7.67 (d, J=8.4 Hz, 1H), 7.49 (d, J=8.4 Hz, 2H), 7.44-7.27 (m, 6H), 7.04 (dd, J=2.1, 8.1 Hz, 1H), 5.22 (s, 2H), 4.81 and 4.69 (AB, J=18.0 Hz, 2H), 4.24 (t, J=6.2 Hz, 1H), 3.16 (t, J=11.5 Hz, 1H), 3.06-2.90 (m, 2H), 2.75 (t, J=8.3 Hz, 2H), 2.05-2.01 (m, 1H), 1.87-1.74 (m, 2H), 1.71-1.60 (m, 2H), 1.51-1.39 (m, 2H); MS m/z: 432 (M+H)+. | 4.4E-08 |
| 69 | 6-[3-(piperidine-1-carbonyl)-phenyl] | 2-(R)-1-Aza-bicyclo[2.2.2]oct-3-yl-6-[3-(piperidine-1-carbonyl)-phenyl]-2,3-dihydro-isoindol-1-one | Title compound obtained as a tan solid in 63% yield (see Method D for details). ¹H NMR (300.132 MHz, DMSO) δ7.94-7.90 (m, 2H), 7.80 (d, J=8.3 Hz, 1H), 7.71-7.66 (m, 2H), 7.55 (t, J=8.3 Hz, 1H), 7.38 (d, J=12.5 Hz, 1H), 4.81 and 4.69 (AB, J=18.0 Hz, 2H), 4.24 (t, J=8.4 Hz, 1H), 3.67-3.40 (m, 4H), 3.16 (t, J=11.0 Hz, 1H), 3.04-2.87 (m, 2H), 2.75 (t, J=8.2 Hz, 2H), 2.05-1.99 (m, 1H), 1.89-1.77 (m, 1H), 1.72- | 2.3E-08 |

-continued

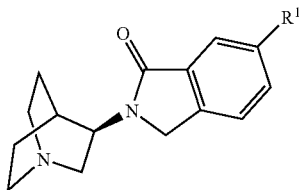

| Ex. | R¹ | Chemical Name | Experimental Data | α7 Ki |
|---|---|---|---|---|
| | | | 1.38 (m, 10H);MS m/z: 430 (M+H)+. | |
| 70 | 6-[3-(pyrrolidine-1-carbonyl)-phenyl] | 2-(R)-1-Aza-bicyclo[2.2.2]oct-3-yl-6-[3-(pyrrolidine-1-carbonyl)-phenyl]-2,3-dihydro-isoindol-1-one | Title compound obtained as a tan solid in 70% yield (see Method D for details). ¹H NMR (300.132 MHz, DMSO) δ7.95-7.90 (m, 2H), 7.83-7.79 (m, 2H), 7.69 (d, J=7.6 Hz, 1H), 7.58-7.49 (m, 2H), 4.81 and 4.70 (AB, J=18.0 Hz, 2H), 4.24 (t, J=7.4 Hz, 1H), 3.53-3.39 (m, 4H), 3.16 (t, J=12.7 Hz, 1H), 3.05-2.91 (m, 2H), 2.75 (t, J=8.0 Hz, 2H), 2.01 (s, 1H), 1.90-1.77 (m, 6H), 1.73-1.58 (m, 3H), 1.49-1.37 (m, 1H); MS m/z: 416 (M+H)+. | 1.4E-08 |
| 71 | 6-(3-dimethylamino-phenyl) | 2-(R)-1-Aza-bicyclo[2.2.2]oct-3-yl-6-(3-dimethylamino-phenyl)-2,3-dihydro-isoindol-1-one | Title compound obtained as a tan solid in 58% yield (see Method D for details). ¹H NMR (300.132 MHz, DMSO) δ7.89-7.83 (m, 2H), 7.65 (d, J=8.0 Hz, 1H), 7.28 (t, J=8.0 Hz, 1H), 6.97-6.94 (m, 2H), 6.78-6.74 (m, 1H), 4.78 and 4.68 (AB, J=18.0 Hz, 2H), 4.23 (t, J=8.3 Hz, 1H), 3.15 (t, J=12.8 Hz, 1H), 3.05-2.90 (m, 8H), 2.75 (t, J=8.7 Hz, 2H), 2.05-1.99 (m, 1H), 1.87-1.74 (m, 2H), 1.69-1.60 (m, 3H), 1.49-1.38 (m, 1H); MS m/z: 362 (M+H)+. | 4.2E-09 |
| 72 | 6-(3-methylsulfanyl-phenyl) | 2-(R)-1-Aza-bicyclo[2.2.2]oct-3-yl-6-(3-methylsulfanyl-phenyl)-2,3-dihydro-isoindol-1-one | Title compound obtained as a tan solid in 29% yield (see Method D for details). ¹H NMR (300.132 MHz, DMSO) δ7.92-7.87 (m, 2H), 7.68 (d, J=8.3 Hz, 1H), 7.56 (s, 1H), 7.50-7.39 (m, 2H), 7.29 (d, J=7.9 Hz, 1H), 4.79 and 4.67 (q, J=18.0 Hz, 2H), 4.24 (t, J=7.9 Hz, 1H), 3.15 (t, J=12.1 Hz, 1H), 3.04-2.89 (m, 2H), 2.75 (t, J=7.0 Hz, 2H), 2.55 (s, 3H), 2.02 (s, 1H), 1.88-1.75 (m, 2H), 1.73-1.58 (m, 2H), 1.48-1.38 (m, 2H); MS m/z: 365 (M+H)+. | 3.7E-08 |

What is claimed is:

1. A compound in accord with formula II:

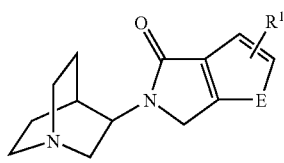

wherein:

E represents or $CH_2$, NH, O or S;

$R^1$ is selected from hydrogen, halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —$C_1$-$C_6$alkyl, —$C_3$-$C_6$cycloalkyl, —$C_1$-$C_6$alkoxy, —$C_2$-$C_6$alkenyl, —$C_2$-$C_6$alkynyl, halogen, —CN, —$NO_2$, —CF3, —$S(O)_mR^2$ wherein m is 0, 1 or 2, —NR²R³, —NR²(CO)R³, —CH₂NR²R³, OR², —CH₂OR², —C(O)NR²R³, or —CO₂R⁴;

R² and R³ are independently selected at each occurrence from hydrogen, —C₁-C₄alkyl, —C₁- C₄alkoxy, —C₃-C₆cycloalkyl, aryl, heteroaryl, —C(O)R⁴, —CO₂R⁴ or —SO₂R⁴, or R² and R³ in combination is —(CH₂)ⱼG(CH₂)ₖ— or -G(CH₂)ⱼG- wherein G is oxygen, sulfur, NR⁴, or a bond, j is 0, 1, 2, 3 or 4 and k is 0, 1, 2, 3 or 4, and R⁴ is independently selected at each occurrence from hydrogen, —C₁-C₄alkyl, aryl, or heteroaryl;

or a stereoisomer, enantiomer, in vivo-hydrolysable precursor or pharmaceutically-acceptable salt thereof.

2. A compound in accord with formula III:

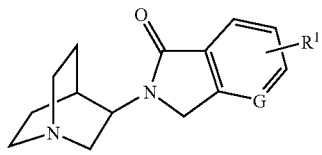

III wherein:
G represents CH or N;
R¹ is selected from halogen or a substituted or unsubstituted 5- or 6-membered aromatic or heteroaromatic ring having 0, 1 or 2 nitrogen atoms, 0 or 1 oxygen atoms, and 0 or 1 sulfur atoms, or selected from a substituted or unsubstituted 8-, 9- or 10-membered fused aromatic or heteroaromatic ring system having 0, 1, 2 or 3 nitrogen atoms, 0 or 1 oxygen atoms, and 0 or 1 sulfur atoms, said aromatic or heteroaromatic rings or ring systems, when substituted, having substituents selected from —C₁-C₆alkyl, —C₃-C₆cycloalkyl, —C₁-C₆alkoxy, —C₂-C₆alkenyl, —C₂-C₆alkynyl, halogen, —CN, —NO₂, —CF₃, —S(O)ₘR² wherein m is 0, 1 or 2, —NR²R³, —NR²(CO)R³, —CH₂NR²R³, OR², —CH₂OR², —C(O)NR²R³, or —CO₂R⁴;

R² and R³ are independently selected at each occurrence from hydrogen, —C₁C₄alkyl, —C₁- C₄alkoxy, —C₃-C₆cycloalkyl, aryl, heteroaryl, —C(O)R⁴, —CO₂R⁴ or —SO₂R⁴, or R² and R³ in combination is —(CH₂)ⱼG(CH₂)ₖ— or -G(CH₂)ⱼG- wherein G is oxygen, sulfur, NR⁴, or a bond, j is 0, 1, 2 , 3 or 4 and k is 0, 1, 2, 3 or 4, and R⁴ is independently selected at each occurrence from hydrogen, —C₁-C₄alkyl, aryl, or heteroaryl;

or a stereoisomer, enantiomer, in vivo-hydrolysable precursor or pharmaceutically-acceptable salt thereof.

3. A compound according to claim 1, wherein,
R¹ is selected from hydrogen, halogen and substituted or unsubstituted phenyl, pyridyl, quinolinyl, piperazinyl or morpholinyl, said phenyl, pyridyl, quinolinyl, piperazinyl or morpholiny, when substituted, having substituents selected from —C₁-C₆alkyl, —C₃-C₆cycloalkyl, —C₁-C₆alkoxy, —C₂-C₆alkenyl, —C₂-C₆alkynyl, halogen, —CN, —NO₂, —CF₃, —S(O)ₘR² wherein m is 0, 1 or 2, —NR²R³, —CH₂NR²R³, —OR², —CH₂OR² or —CO₂R⁴.

4. A compound according to claim 1, wherein:
said compound is an R-stereoisomer in accord with formula IV

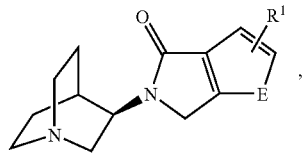

IV or a pharmaceutically-acceptable salt thereof.

5. A compound selected from:
2-(R)-1-Aza-bicyclo[2.2.2]oct-3-yl-6-phenyl-2,3-dihydro-isoindol-1-one;
2-(R)-1-Aza-bicyclo[2.2.2]oct-3-yl-5-(4-methyl-piperazin-1-yl)-2,3-dihydro-isoindol-1-one;
5-(R)-1-Aza-bicyclo[2.2.2]oct-3-yl-2-phenyl-5,6-dihydro-furo[2,3-c]pyrrol-4-one;
2-(R)-1-Aza-bicyclo[2.2.2]oct-3-yl-6-bromo-2,3-dihydro-isoindol-1-one;
2-(R)-1-Aza-bicyclo[2.2.2]oct-3-yl-6-pyridin-3-yl-2,3-dihydro-isoindol-1-one;
2-(R)-1-Aza-bicyclo[2.2.2]oct-3-yl-6-pyridin-4-yl-2,3-dihydro-isoindol-1-one;
2-(R)-1-Aza-bicyclo[2.2.2]oct-3-yl-5-bromo-2,3-dihydro-isoindol-1-one;
2-(R)-1-Aza-bicyclo[2.2.2]oct-3-yl-5-phenyl-2,3-dihydro-isoindol-1-one;
2-(R)-1-Aza-bicyclo[2.2.2]oct-3-yl-5-pyridin-3-yl-2,3-dihydro-isoindol-1-one;
2-(R)-1-Aza-bicyclo[2.2.2]oct-3-yl-5-pyridin-4-yl-2,3-dihydro-isoindol-1-one;
2-(R)-1-Aza-bicyclo[2.2.2]oct-3-yl-4-bromo-2,3-dihydro-isoindol-1-one;
2-(R)-1-Aza-bicyclo[2.2.2]oct-3-yl-4-phenyl-2,3-dihydro-isoindol-1-one;
2-(R)-1-Aza-bicyclo[2.2.2]oct-3-yl-4-pyridin-3-yl-2,3-dihydro-isoindol-1-one;
2-(R)-1-Aza-bicyclo[2.2.2]oct-3-yl-4-pyridin-4-yl-2,3-dihydro-isoindol-1-one;
2-(R)-1-Aza-bicyclo[2.2 2]oct-3-yl-7-bromo-2,3-dihydro-isoindol-1-one;
2-(R)-1-Aza-bicyclo[2.2.2]oct-3-yl-7-phenyl-2,3-dihydro-isoindol-1-one;
2-(R)-1-Aza-bicyclo[2.2.2]oct-3-yl-7-pyridin-3-yl-243-dihydro-isoindol-1-one;
2-(R)-1-Aza-bicyclo[2.2.2]oct-3-yl-7-pyridin-4-yl-2,3-dihydro-isoindol-1-one;
(R)-2-(1-Aza-bicyclo[2.2.2]oct-3-yl)-2,3-dihydro-isoindol-1-one;
2-(R)-1-Aza-bicyclo[2.2.2]oct-3-yl-5-(4-methyl-piperazin-1-yl)-2,3-dihydro-isoindol-1-one;
2-(R)-1-Aza-bicyclo[2.2.2]oct-3-yl-5-morpholin-4-yl-2,3-dihydro-isoindol-1-one;
5-(R)-1-Aza-bicyclo[2.2.2]oct-3-yl-2-bromo-5,6-dihydro-furo[2,3-c]pyrrol-4-one;
5-(R)-1-Aza-bicyclo[2.2.2]oct-3-yl-2-phenyl-5,6-dihydro-furo[2,3-c]pyrrol-4-one;
5-(R)-1-Aza-bicyclo[2.2.2]oct-3-yl-2-pyridin-3-yl-5,6-dihydro-furo[2,3-c]pyrrol-4-one;
5-(R)-1-Aza-bicyclo[2.2.2]oct-3-yl-2-pyridin-4-yl-5,6-dihydro-furo[2,3-c]pyrrol-4-one;
2-(R)-1-Aza-bicyclo[2.2.2]oct-3-yl-6-(3-Chloro-phenyl)-2,3-dihydro-isoindol-1-one;
2-(R)-1-Aza-bicyclo[2.2.2]oct-3-yl-6-(4-Chloro-phenyl)-2,3-dihydro-isoindol-1-one;

2-(R)-1-Aza-bicyclo[2.2.2]oct-3-yl-6-quinolin-8-yl-2,3-dihydro-isoindol-1-one;

2-(R)-1-Aza-bicyclo[2.2.2]oct-3-yl-6-benzo [1,3]dioxol-5-yl-2,3-dihydro-isoindol-1-one;

2-(R)-1-Aza-bicyclo[2.2.2]oct-3-yl-6-(2-Chloro-phenyl)-2,3-dihydro-isoindol-1-one;

2-(R)-1-Aza-bicyclo[2.2.2]oct-3-yl-6-(2-methoxy-phenyl)-2,3-dihydro-isoindol-1-one; N-[3-((R)-2-1-Aza-bicyclo[2.2.2]oct-3-yl-3-oxo-2,3-dihydro-1H-isoindol-5-yl)-phenyl]-acetamide;

2-(R)-1-Aza-bicyclo[2.2.2]oct-3-yl-6-morpholin-4-yl-2,3-dihydro-isoindol-1-one, 4-((R)-2-1-Aza-bicyclo[2.2.2]oct-3-yl-3-oxo-2,3-dihydro-1H-isoindol-5-yl)-N,N-dimethyl-benzamide; or a pharamaceutically acceptable salt thereof.

6. A compound according to claim 1, wherein one or more of the atoms is a radioisotope of the same atom.

7. A compound according to claim 1 or 2, additionally comprising one or more atoms selected from tritium, $^{18}F$, $^{123}I$, $^{125}I$, $^{131}I$, $^{75}Br$, $^{76}Br$, $^{77}Br$ or $^{82}Br$.

8. A pharmaceutical composition comprising a compound according to claim 1 or 2 and a pharmaceutically-acceptable diluent, lubricant or carrier.

9. A compound according to claim 2, wherein:
said compound is an R-stereoisomer in accord with formula V,

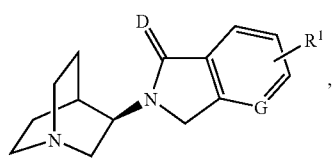

V or pharmaceutically-acceptable salt thereof.

* * * * *